US011395668B2

(12) United States Patent
Girdhar et al.

(10) Patent No.: US 11,395,668 B2
(45) Date of Patent: Jul. 26, 2022

(54) ELECTRICALLY ENHANCED RETRIEVAL OF MATERIAL FROM VESSEL LUMENS

(71) Applicant: Covidien LP, Mansfield, MA (US)

(72) Inventors: Gaurav Girdhar, Ladera Ranch, CA (US); Hoai Nguyen, Westminster, CA (US); Dinh Nguyen, Garden Grove, CA (US)

(73) Assignee: COVIDIEN LP, Mansfield, MA (US)

( * ) Notice: Subject to any disclaimer, the term of this patent is extended or adjusted under 35 U.S.C. 154(b) by 285 days.

(21) Appl. No.: 16/711,862

(22) Filed: Dec. 12, 2019

(65) Prior Publication Data

US 2021/0177442 A1   Jun. 17, 2021

(51) Int. Cl.
| A61B 17/221 | (2006.01) |
| A61F 2/95 | (2013.01) |
| A61B 17/22 | (2006.01) |
| A61B 90/00 | (2016.01) |

(52) U.S. Cl.
CPC ............ *A61B 17/221* (2013.01); *A61B 90/39* (2016.02); *A61F 2/95* (2013.01); *A61B 2017/2215* (2013.01); *A61B 2017/22034* (2013.01); *A61B 2017/22035* (2013.01); *A61B 2090/3966* (2016.02); *A61F 2002/9528* (2013.01)

(58) Field of Classification Search
CPC ................. A61F 2/95; A61F 2002/9528; A61F 2002/9534; A61B 17/221; A61B 2017/22034; A61B 2017/22035; A61B 2017/2215; A61B 17/22031
See application file for complete search history.

(56) References Cited

U.S. PATENT DOCUMENTS

| 5,549,626 A | 8/1996 | Miller et al. |
| 5,928,260 A | 7/1999 | Chin et al. |
| 5,972,019 A | 10/1999 | Engelson et al. |

(Continued)

FOREIGN PATENT DOCUMENTS

| EP | 1484025 A1 | 12/2004 |
| EP | 2319575 B1 | 11/2013 |

(Continued)

OTHER PUBLICATIONS

Extended European Search Report dated Jul. 15, 2021; European Application No. 18888795.4; 6 pages.

(Continued)

*Primary Examiner* — Wade Miles
(74) *Attorney, Agent, or Firm* — Fortem IP LLP; Matthew Lincicum

(57) ABSTRACT

Retrieval of material from vessel lumens can be improved by electrically enhancing attachment of the material to a medical device. The device can include an elongate core member having a distal portion configured to be intravascularly positioned at a treatment site within a blood vessel lumen, and an interventional element connected to the distal portion of the elongate core member. The interventional element includes a body that is expandable from a first configuration to a second configuration and an electrically conductive radiopaque marker coupled to the body. An electrically conductive lead has a distal portion electrically coupled to the radiopaque marker and a proximal portion configured to be electrically coupled to a current source.

17 Claims, 15 Drawing Sheets

(56) References Cited

U.S. PATENT DOCUMENTS

| | | |
|---|---|---|
| 6,022,336 A | 2/2000 | Zadno-Azizi et al. |
| 6,059,779 A | 5/2000 | Mills |
| 6,315,794 B1 | 11/2001 | Richter |
| 6,540,733 B2 | 4/2003 | Constantz et al. |
| 6,663,650 B2 | 12/2003 | Sepetka et al. |
| 7,094,249 B1 | 8/2006 | Broome et al. |
| 7,556,624 B2 | 7/2009 | Laufer et al. |
| 8,038,674 B2 | 10/2011 | Schmaltz et al. |
| 8,382,821 B2 | 2/2013 | Richter |
| 8,603,014 B2 | 12/2013 | Alleman et al. |
| 8,837,800 B1 | 9/2014 | Bammer et al. |
| 8,888,788 B2 | 11/2014 | Adams et al. |
| 8,965,534 B2 | 2/2015 | Hyatt et al. |
| 9,011,431 B2 | 4/2015 | Long et al. |
| 9,039,753 B2 | 5/2015 | Thramann |
| 9,119,656 B2 | 9/2015 | Bose et al. |
| 9,126,018 B1 | 9/2015 | Garrison |
| 9,179,971 B2 | 11/2015 | Kirschenman |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,681,882 B2 | 6/2017 | Wilson et al. |
| 9,713,730 B2 | 7/2017 | Mathur et al. |
| 9,737,318 B2 | 8/2017 | Monstadt et al. |
| 9,770,251 B2 | 9/2017 | Bowman et al. |
| 9,795,400 B2 | 10/2017 | Davidson |
| 9,801,643 B2 | 10/2017 | Hansen et al. |
| 9,808,271 B2 | 11/2017 | Ulm |
| 9,827,084 B2 | 11/2017 | Bonnette et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,092,241 B2 | 10/2018 | Toth et al. |
| 10,251,569 B2 | 4/2019 | Burkett |
| 10,987,117 B2 | 4/2021 | Girdhar et al. |
| 11,058,444 B2 | 7/2021 | Girdhar et al. |
| 11,090,071 B2 | 8/2021 | Girdhar et al. |
| 11,160,571 B2 | 11/2021 | Nguyen et al. |
| 2001/0001314 A1 | 5/2001 | Davison et al. |
| 2002/0091407 A1 | 7/2002 | Zadno-Azizi et al. |
| 2002/0133111 A1 | 9/2002 | Shadduck et al. |
| 2003/0088245 A1 | 5/2003 | Woloszko et al. |
| 2003/0135232 A1 | 7/2003 | Douk et al. |
| 2004/0219660 A1 | 11/2004 | Dev et al. |
| 2006/0089638 A1 | 4/2006 | Carmel et al. |
| 2008/0045881 A1 | 2/2008 | Teitelbaum et al. |
| 2008/0262489 A1 | 10/2008 | Steinke et al. |
| 2008/0294181 A1 | 11/2008 | Wensel et al. |
| 2009/0054918 A1 | 2/2009 | Henson |
| 2009/0069828 A1 | 3/2009 | Martin et al. |
| 2009/0112228 A1 | 4/2009 | Deshpande et al. |
| 2009/0198269 A1 | 8/2009 | Hannes et al. |
| 2009/0318892 A1 | 12/2009 | Aboytes et al. |
| 2009/0318943 A1* | 12/2009 | Eidenschink ........ A61N 1/3627 606/167 |
| 2010/0004623 A1 | 1/2010 | Hamilton et al. |
| 2010/0042136 A1 | 2/2010 | Berrada et al. |
| 2010/0228280 A1 | 9/2010 | Groothuis et al. |
| 2010/0256627 A1 | 10/2010 | Ma et al. |
| 2011/0196478 A1 | 8/2011 | Torosoff |
| 2011/0202085 A1 | 8/2011 | Loganathan et al. |
| 2011/0301549 A1 | 12/2011 | Hartmann |
| 2011/0301594 A1 | 12/2011 | Orion et al. |
| 2012/0101560 A1 | 4/2012 | Kluck |
| 2013/0030461 A1 | 1/2013 | Marks et al. |
| 2013/0072960 A1 | 3/2013 | Schneider et al. |
| 2013/0281788 A1 | 10/2013 | Garrison |
| 2013/0282084 A1 | 10/2013 | Mathur et al. |
| 2013/0317589 A1 | 11/2013 | Martin et al. |
| 2013/0345739 A1 | 12/2013 | Brady et al. |
| 2014/0025152 A1 | 1/2014 | Headley |
| 2014/0172001 A1 | 6/2014 | Becking et al. |
| 2014/0276074 A1 | 9/2014 | Warner |
| 2014/0277013 A1 | 9/2014 | Sepetka et al. |
| 2014/0277079 A1 | 9/2014 | Vale et al. |
| 2014/0309673 A1 | 10/2014 | Dacuycuy et al. |
| 2014/0309675 A1 | 10/2014 | Maisano et al. |
| 2014/0343595 A1 | 11/2014 | Monstadt et al. |
| 2014/0364896 A1 | 12/2014 | Consigny |
| 2015/0112321 A1 | 4/2015 | Cadouri |
| 2015/0133990 A1 | 5/2015 | Davidson |
| 2015/0150672 A1 | 6/2015 | Ma |
| 2015/0297251 A1 | 10/2015 | Sos |
| 2015/0359547 A1 | 12/2015 | Vale et al. |
| 2016/0008003 A1 | 1/2016 | Kleshinski et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0228681 A1 | 8/2016 | Di Palma et al. |
| 2016/0228684 A1 | 8/2016 | Martin |
| 2016/0296690 A1 | 10/2016 | Kume et al. |
| 2016/0302808 A1 | 10/2016 | Loganathan et al. |
| 2016/0331377 A1 | 11/2016 | Divino et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0215955 A1 | 8/2017 | Hancock et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2017/0367707 A1 | 12/2017 | Divino |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0133436 A1 | 5/2018 | Garrison et al. |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0161514 A1 | 6/2018 | Rothenberg et al. |
| 2018/0161541 A1 | 6/2018 | Haldis et al. |
| 2018/0185614 A1 | 7/2018 | Garrison et al. |
| 2018/0200040 A1 | 7/2018 | Wasdyke et al. |
| 2018/0236221 A1 | 8/2018 | Opie et al. |
| 2018/0303595 A1 | 10/2018 | Opie et al. |
| 2018/0344970 A1 | 12/2018 | Kornowski et al. |
| 2019/0038438 A1 | 2/2019 | John et al. |
| 2019/0046119 A1 | 2/2019 | Oxley |
| 2019/0175199 A1 | 6/2019 | Girdhar et al. |
| 2019/0175200 A1 | 6/2019 | Girdhar et al. |
| 2019/0262069 A1 | 8/2019 | Taff et al. |
| 2019/0388097 A1 | 12/2019 | Girdhar et al. |
| 2019/0388107 A1 | 12/2019 | Girdhar et al. |
| 2019/0388111 A1 | 12/2019 | Nguyen et al. |
| 2019/0388112 A1 | 12/2019 | Nguyen et al. |
| 2020/0054392 A1 | 2/2020 | Whiteley et al. |
| 2020/0129742 A1 | 4/2020 | Cope et al. |
| 2020/0297367 A1 | 9/2020 | Girdhar et al. |
| 2020/0297410 A1 | 9/2020 | Nguyen et al. |
| 2020/0390455 A1 | 12/2020 | Nguyen et al. |

(56) References Cited

U.S. PATENT DOCUMENTS

| | | |
|---|---|---|
| 2020/0390456 A1 | 12/2020 | Nguyen et al. |
| 2020/0390457 A1 | 12/2020 | Nageswaran et al. |
| 2020/0390458 A1 | 12/2020 | Nguyen et al. |
| 2021/0068853 A1 | 3/2021 | Nguyen et al. |
| 2021/0177427 A1 | 6/2021 | Nguyen et al. |
| 2021/0177446 A1 | 6/2021 | Girdhar et al. |
| 2021/0186540 A1 | 6/2021 | Taff et al. |
| 2021/0267612 A1 | 9/2021 | Girdhar et al. |
| 2022/0022899 A1 | 1/2022 | Girdhar et al. |
| 2022/0022900 A1 | 1/2022 | Nguyen et al. |

FOREIGN PATENT DOCUMENTS

| | | |
|---|---|---|
| EP | 2490764 B1 | 9/2014 |
| EP | 2967605 A1 | 1/2016 |
| EP | 3184067 A1 | 6/2017 |
| JP | 10290805 A | 11/1998 |
| JP | 2014004219 A | 1/2014 |
| JP | 2018118132 A | 8/2018 |
| KR | 20180102877 A | 9/2018 |
| WO | 2010061376 A1 | 6/2010 |
| WO | 2014079148 A1 | 5/2014 |
| WO | 2015141317 A1 | 9/2015 |
| WO | 2016198947 A1 | 12/2016 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018127796 A1 | 7/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 201818///6 A1 | 10/2018 |
| WO | 2019102307 A1 | 5/2019 |
| WO | 2019246377 A2 | 12/2019 |

OTHER PUBLICATIONS

International Search Report and Written Opinion dated Feb. 26, 2021; International Application No. PCT/US20/63200; 14 pages.

International Search Report and Written Opinion dated Nov. 3, 2020, International Application No. PCT/US20/70142, 18 pages.

Fort, Stephen, et al., "'Fused-Gold' vs. 'Bare' stainless steelNIRflex stents of the same geometric design in diseased native coronary arteries. Long-term results from the NIR Top Study", Euro Interv 2007; 3:256-261.

International Search Report and Written Opinion dated May 25, 2020, International Application No. PCT/US20/22463, 10 pages.

* cited by examiner

ELECTRICALLY ENHANCED RETRIEVAL OF MATERIAL FROM VESSEL LUMENS

TECHNICAL FIELD

The present technology relates generally to devices and methods for removing obstructions from body lumens. Some embodiments of the present technology relate to devices and methods for electrically enhanced removal of clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (i.e., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. The treatment systems of the present technology provide an interventional element carrying one or more electrodes and a current generator configured to positively charge the interventional element during one or more stages of a thrombectomy procedure. For example, the current generator may apply a constant or pulsatile direct current (DC) to the electrodes. The positively charged electrodes and/or interventional element attract negatively charged blood components, thereby improving attachment of the thrombus to the interventional element and reducing the number of device passes or attempts necessary to fully retrieve the clot.

One approach to delivering current to an interventional element is to conduct current along a core wire coupled to a proximal end of the interventional element. However, the inventors have discovered that this approach can lead to disadvantageous concentration of electrical charge along a proximal portion of the interventional element, with insufficient charge density in more distal portions of the interventional element (e.g., along some or all of the working length of the interventional element). This is particularly true of interventional elements having a proximal portion that tapers to a connection point with the core wire. This concentration of current in the proximal portion can reduce the efficacy of electrostatic enhancement of clot adhesion, as the mechanical clot engagement occurs primarily at a location distal to the region at which the charge density is greatest. Additionally, delivery of current in this manner may require a hypotube or other additional structural element to be coupled to the core wire, thereby stiffening the core assembly and rendering navigability of torturous vasculature more difficult.

To overcome these and other problems, in some aspects of the present technology a treatment system can include one or more electrodes carried by or otherwise coupled to the interventional element. The electrodes can take the form of radiopaque markers affixed to a portion of the interventional element, and can be arranged so as to improve charge distribution over the surface of the interventional element during treatment. For example, by delivering current to electrodes affixed to the interventional element, electrical charge can be concentrated in select regions of the interventional element (e.g., regions adjacent to the delivery electrodes).

Current can flow to the delivery electrodes over a plurality of electrical leads extending between the current generator (which may be positioned extracorporeally) and the electrodes. One or more return electrodes can likewise be coupled to the interventional element, and optionally may also double as radiopaque marker(s). Additionally or alternatively, the return electrode(s) may be positioned elsewhere (e.g., a needle, a grounding pad, a conductive element carried by a one or more catheters of the treatment system, a guide wire, and/or any other suitable conductive element configured to complete an electrical circuit with the delivery electrodes and an extracorporeally positioned current generator). When the interventional element is placed in the presence of blood (or any other electrolytic medium) and voltage is applied at the terminals of the current generator, current flows along the leads to the delivery electrodes and to the interventional element, through the blood, and to the return electrode(s), thereby positively charging at least a portion of the interventional element and adhering clot material thereto.

The treatment systems and methods of the present technology can further improve adhesion of the clot to the interventional element by positioning the delivery electrodes with respect to the interventional element in a manner that improves charge distribution, and/or by modifying characteristics of the interventional element. For example, in some embodiments, some or all of the interventional element can be coated with one or more highly conductive materials, such as gold, to improve clot adhesion. In some aspects of the present technology, a working length of the interventional element may be coated with the conductive material while a non-working length of the interventional element may be coated with an insulative material.

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A medical device comprising:
   an elongate core member having a distal portion configured to be intravascularly positioned at a treatment site within a blood vessel lumen; and
   an interventional element coupled to the distal portion of the core member, the interventional element comprising:
      a body that is expandable from a first configuration to a second configuration;
      a radiopaque element coupled to the body, the radiopaque element comprising an electrically conductive material;
      an electrically conductive lead having a distal portion electrically coupled to the radiopaque element and a proximal portion configured to be electrically coupled to a current source.

2. The device of Clause 1, wherein the body comprises an electrically conductive material.

3. The device of any of the preceding Clauses, wherein the body is in electrical communication with the radiopaque element.

4. The device of any of the preceding Clauses, wherein the conductive lead is electrically insulated along at least a portion of its length.

5. The device of any of the preceding Clauses, wherein the conductive lead extends proximally along the core member.

6. The device of any of the preceding Clauses, wherein the conductive lead and the core member are coupled together along at least a portion of their respective lengths.

7. The device of any of the preceding Clauses, wherein the conductive lead comprises at least one of: copper or nitinol.

8. The device of any of the preceding Clauses, wherein the conductive lead comprises a wire having a diameter of between about 0.005 and 0.02 mm.

9. The device of any of the preceding Clauses, wherein the radiopaque element comprises a coil coupled to a portion of the body.

10. The device of any of the preceding Clauses, wherein the radiopaque element is coupled to a distally extending tip of the body.

11. The device of any of the preceding Clauses, wherein the body comprises a plurality of struts forming a plurality of cells, and wherein the radiopaque element is coupled to one of the struts.

12. The device of any of the preceding Clauses, wherein the body comprises a plurality of struts forming a plurality of cells, and wherein the radiopaque element is coupled to a projection extending from one of the struts.

13. The device of any of the preceding Clauses, wherein the radiopaque element comprises a band.

14. The device of any of the preceding Clauses, further comprising:
   a plurality of radiopaque elements coupled to the body, each comprising an electrically conductive material; and
   a plurality of electrically conductive leads, each having a distal portion electrically coupled to one of the plurality of radiopaque elements and having a proximal portion configured to be electrically coupled to the current source.

15. The device of any of the preceding Clauses, wherein the plurality of electrically conductive leads are bundled together along at least a portion of their respective lengths.

16. The device of any of the preceding Clauses, wherein a first set of the plurality of radiopaque elements are configured to serve as delivery electrodes, and wherein a second set of the plurality of radiopaque elements are configured to serve as return electrodes.

17. The device of any of the preceding Clauses, wherein the delivery electrodes are disposed within a working length of the body, and wherein the return electrodes are disposed within a non-working length of the body.

18. The device of any of the preceding Clauses, wherein the delivery electrodes are disposed proximal to the return electrodes.

19. The device of any of the preceding Clauses, wherein the plurality of radiopaque elements are configured to serve as delivery electrodes, the device further comprising a return electrode configured to be coupled to the current source.

20. The device of any of the preceding Clauses, wherein the radiopaque element is configured to serve as a delivery electrode, and wherein the conductive lead is a first conductive lead, the device further comprising:
   a return electrode; and
   a second electrically conductive lead having a distal portion electrically coupled to the return electrode and a proximal portion configured to be electrically coupled to the current source.

21. The device of any of the preceding Clauses, wherein the return electrode comprises a needle or grounding pad.

22. The device of any of the preceding Clauses, wherein the return electrode comprises an exposed conductive member disposed adjacent a proximal portion of the interventional element.

23. The device of any of the preceding Clauses, wherein the exposed conductive member is not carried by the body.

24. The device of any of the preceding Clauses, wherein the radiopaque element is a first radiopaque element, and the return electrode comprises a second radiopaque element coupled to the body and comprising an electrically conductive material.

25. The device of any of the preceding Clauses, wherein the first radiopaque element is disposed within a working length of the body, and wherein the second radiopaque element is disposed within a non-working length of the body.

26. The device of any of the preceding Clauses, wherein the first radiopaque element and the second radiopaque element are each disposed within a working length of the body.

27. The device of any of the preceding Clauses, wherein the first radiopaque element is disposed within a central portion of the body, and wherein the second radiopaque element is disposed at a distal portion of the body.

28. The device of any of the preceding Clauses, wherein the first conductive lead and the second conductive lead each extend proximally alongside the core member.

29. The device of any of the preceding Clauses, wherein the first conductive lead, the second conductive lead, and the core member are non-slidably coupled together along at least a portion of their respective lengths.

30. The device of any of the preceding Clauses, wherein the first conductive lead, the second conductive lead, and the core member are bundled together along at least a portion of their respective lengths.

31. The device of any of the preceding Clauses, wherein the radiopaque element comprises a radiopaque marker.

32. The device of any of the preceding Clauses, wherein the current source comprises a current generator.

33. The device of any of the preceding Clauses, wherein the interventional element comprises a thrombectomy device.

34. The device of any of the preceding Clauses, wherein the interventional element comprises a stent retriever.

35. The device of any of the preceding Clauses, wherein the interventional element comprises a removal device.

36. The device of any of the preceding Clauses, wherein a portion of the interventional element is coated with a conductive material.

37. The device of any of the preceding Clauses, wherein the conductive material comprises gold.

38. The device of any of the preceding Clauses, wherein a portion of the interventional element is coated with a non-conductive material.

39. The device of any of the preceding Clauses, wherein the non-conductive material comprises parylene.

40. A system comprising:
   the device of any of the preceding Clauses; and
   a current source electrically coupled to the electrically conductive lead.

41. A medical device comprising:
   a thrombectomy element comprising:
      a body configured to engage a thrombus; and
      an electrically conductive radiopaque element coupled to the body; and
   an electrically conductive lead in electrical communication with the radiopaque element, the lead configured to be electrically coupled to a current source.

42. The device of any of the preceding Clauses, wherein the body comprises an electrically conductive material.

43. The device of any of the preceding Clauses, wherein the body is in electrical communication with the radiopaque element.

44. The device of any of the preceding Clauses, wherein the conductive lead is electrically insulated along at least a portion of its length.

45. The device of any of the preceding Clauses, wherein the radiopaque element comprises a radiopaque marker.

46. The device of any of the preceding Clauses, wherein the radiopaque element comprises a coil wrapped around a portion of the body.

47. The device of any of the preceding Clauses, wherein the radiopaque element is coupled to a distal tip of the body.

48. The device of any of the preceding Clauses, wherein the body comprises a plurality of struts forming a plurality of cells, and wherein the radiopaque element is coupled to one of the struts.

49. The device of any of the preceding Clauses, wherein the body comprises a plurality of struts forming a plurality of cells, and wherein the radiopaque element is coupled to a projection extending from one of the struts.

50. The device of any of the preceding Clauses, wherein the radiopaque element comprises a band.

51. The device of any of the preceding Clauses, further comprising:
   a plurality of electrically conductive radiopaque elements coupled to the body; and
   a plurality of electrically conductive leads, each electrically coupled to one of the plurality of radiopaque elements and being configured to be electrically coupled to the current source.

52. The device of any of the preceding Clauses, wherein the plurality of electrically conductive leads are bundled together along at least a portion of their respective lengths.

53. The device of any of the preceding Clauses, wherein a first set of the plurality of radiopaque elements are configured to serve as delivery electrodes, and wherein a second set of the plurality of radiopaque elements are configured to serve as return electrodes.

54. The device of any of the preceding Clauses, wherein the delivery electrodes are disposed within a working length of the body, and wherein the return electrodes are disposed within a non-working length of the body.

55. The device of any of the preceding Clauses, wherein the plurality of radiopaque elements are configured to serve as delivery electrodes, the device further comprising a return electrode configured to be coupled to the current source.

56. The device of any of the preceding Clauses, wherein the radiopaque element is configured to serve as a delivery electrode, and wherein the conductive lead is a first conductive lead, the device further comprising:
   a return electrode; and
   a second electrically conductive lead having a distal portion electrically coupled to the return electrode and a proximal portion configured to be electrically coupled to the current source.

57. The device of any of the preceding Clauses, wherein the return electrode comprises a needle or grounding pad.

58. The device of any of the preceding Clauses, wherein the return electrode comprises an exposed conductive member disposed adjacent a proximal portion of the thrombectomy element.

59. The device of any of the preceding Clauses, wherein the exposed conductive member is not carried by the body.

60. The device of any of the preceding Clauses, wherein the radiopaque element is a first radiopaque element, and the return electrode comprises a second radiopaque element coupled to the body and comprising an electrically conductive material.

61. The device of any of the preceding Clauses, wherein the first radiopaque element is disposed within a working length of the body, and wherein the second radiopaque element is disposed within a non-working length of the body.

62. The device of any of the preceding Clauses, wherein the first radiopaque element and the second radiopaque element are each disposed within a working length of the body.

63. The device of any of the preceding Clauses, wherein the first radiopaque element is disposed within a central portion of the body, and wherein the second radiopaque element is disposed at a distal portion of the body.

64. The device of any of the preceding Clauses, wherein the current source comprises a current generator.

65. The device of any of the preceding Clauses, wherein the thrombectomy element comprises a stent retriever.

66. The device of any of the preceding Clauses, wherein a portion of the thrombectomy element is coated with a conductive material.

67. The device of any of the preceding Clauses, wherein a portion of the thrombectomy element is coated with a non-conductive material.

68. A method, comprising:
   advancing a thrombectomy device through a catheter to an intravascular treatment site, the thrombectomy device comprising:
      a body that is expandable from a first configuration to a second configuration;
      a radiopaque element coupled to the body, the radiopaque element comprising an electrically conductive material; and
   supplying electrical current to the radiopaque element.

69. The method of any of the preceding Clauses, wherein supplying electrical current to the radiopaque element causes current to pass to the thrombectomy device.

70. The method of any of the preceding Clauses, wherein the thrombectomy device comprises an electrically conductive material.

71. The method of any of the preceding Clauses, wherein the thrombectomy device further comprises a plurality of radiopaque elements coupled to the body and comprising an electrically conductive material, the method further comprising supplying electrical current to the plurality of radiopaque elements.

72. The method of any of the preceding Clauses, wherein the radiopaque element is coupled to a projection extending from a strut of the body.

73. The method of any of the preceding Clauses, wherein the radiopaque element is coupled to a distally extending tip of the body.

74. The method of any of the preceding Clauses, wherein the radiopaque element comprises at least one of: a coil or a band.

75. The method of any of the preceding Clauses, wherein the radiopaque element comprises a radiopaque marker.

76. The method of any of the preceding Clauses, wherein supplying current produces a positive charge along at least a portion of the body.

77. The method of any of the preceding Clauses, further comprising concentrating the positive charge along a working length of the body, wherein a proximal end of the working length is distal of a proximal end of the body and a distal end of the working length is proximal of a distal end of the body.

78. The method of any of the preceding Clauses, wherein supplying electrical current includes delivering a direct current to the radiopaque element.

79. The method of any of the preceding Clauses, wherein supplying electrical current includes delivering a pulsatile current to the radiopaque element.

80. The method of any of the preceding Clauses, wherein supplying electrical current includes delivering a current to the radiopaque element, the current having an amplitude of between about 0.5 mA and about 5 mA.

81. The method of any of the preceding Clauses, wherein supplying electrical current includes delivering a current to the radiopaque element, the current having an amplitude of about 2 mA.

82. The method of any of the preceding Clauses, wherein the thrombectomy device comprises a stent retriever.

83. The method of any of the preceding Clauses, wherein the thrombectomy device is a laser-cut stent or a mesh.

84. A thrombectomy device comprising:
   a body that is expandable from a first configuration to a second configuration, the body having a working length portion and a non-working length portion disposed proximal of the working length portion;
   one or more electrodes coupled to the body within the working length portion;
   one or more conductive leads electrically coupled to the one or more electrodes, the conductive lead(s) configured to be electrically coupled to a current source,
   wherein the electrode(s) are configured such that, when current is supplied to the conductive lead(s) via the current source, an electrical charge density is greater in the working-length portion than in the non-working length portion.

85. The device of any of the preceding Clauses, wherein the non-working length portion comprises a proximally tapering segment, and wherein the working-length portion comprises a non-tapering segment.

86. The device of any of the preceding Clauses, wherein the working length portion comprises a segment of the body configured to mechanically engage with a thrombus.

87. The device of any of the preceding Clauses, wherein the one or more electrodes are radiopaque.

88. The device of any of the preceding Clauses, wherein the one or more electrodes comprise platinum, gold, or copper.

89. The device of any of the preceding Clauses, wherein the one or more electrodes comprise a coil, band, cap, or tube.

90. The device of any of the preceding Clauses, wherein the body comprises a plurality of struts forming a plurality of cells, and wherein the one or more of the electrodes are coupled to one of the struts.

91. The device of any of the preceding Clauses, wherein the body comprises a plurality of struts forming a plurality of cells, and wherein one or more of the electrodes is coupled to a projection extending from one of the struts.

92. The device of any of the preceding Clauses, wherein the body comprises an electrically conductive material.

93. The device of any of the preceding Clauses, wherein the body is in electrical communication with the one or more electrodes.

94. The device of any of the preceding Clauses, wherein the body comprising an electrically conductive material.

95. The device of any of the preceding Clauses, wherein the one or more electrodes are electrically coupled to the body within the working length portion.

96. The device of any of the preceding Clauses, wherein the conductive lead is electrically insulated along at least a portion of its length.

97. The device of any of the preceding Clauses, further comprising:
   a plurality of electrodes coupled to the body; and
   a plurality of electrically conductive leads, each electrically coupled to one of the plurality of electrodes and being configured to be electrically coupled to the current source.

98. The device of any of the preceding Clauses, wherein the plurality of electrically conductive leads are bundled together along at least a portion of their respective lengths.

99. The device of any of the preceding Clauses, wherein a first set of the plurality of electrodes are configured to serve as delivery electrodes, and wherein a second set of the plurality of electrodes are configured to serve as return electrodes.

100. The device of any of the preceding Clauses, wherein the delivery electrodes are disposed within a working length of the body, and wherein the return electrodes are disposed within a non-working length of the body.

101. The device of any of the preceding Clauses, wherein the plurality of electrodes are configured to serve as delivery electrodes, the device further comprising a return electrode configured to be coupled to the current source.

102. The device of any of the preceding Clauses, wherein the one or more electrodes are configured to serve as delivery electrodes, and wherein the conductive lead is a first conductive lead, the device further comprising:
   a return electrode; and
   a second electrically conductive lead having a distal portion electrically coupled to the return electrode and a proximal portion configured to be electrically coupled to the current source.

103. The device of any of the preceding Clauses, wherein the return electrode comprises a needle or grounding pad.

104. The device of any of the preceding Clauses, wherein the return electrode comprises an exposed conductive member disposed adjacent a proximal portion of the body.

105. The device of any of the preceding Clauses, wherein the exposed conductive member is not carried by the body.

106. The device of any of the preceding Clauses, wherein the return electrode comprises a radiopaque marker coupled to the body and comprising an electrically conductive material.

107. The device of any of the preceding Clauses, wherein the delivery electrode is disposed within a working length of the body, and wherein the return electrode is disposed within a non-working length of the body.

108. The device of any of the preceding Clauses, wherein the delivery electrode and the return electrode are each disposed within a working length of the body.

109. The device of any of the preceding Clauses, wherein the body comprises a stent retriever.

110. The device of any of the preceding Clauses, wherein a portion of the body is coated with a conductive material.

111. The device of any of the preceding Clauses, wherein a portion of the body is coated with a non-conductive material.

112. A thrombectomy device comprising:
   a body that is expandable from a first configuration to a second configuration, the body having a proximal tapering portion and a distal portion;
   a plurality of electrodes coupled to the body;
   a plurality of conductive leads electrically coupled to the electrodes, the conductive leads configured to be electrically coupled to a current source,
   wherein the electrodes are configured such that, when current is supplied to the conductive leads via the current source, an electrical charge density is greater in the distal portion than in the proximal tapering portion.

113. The device of any of the preceding Clauses, wherein the electrodes are radiopaque.

114. The device of any of the preceding Clauses, wherein the electrodes comprise platinum, gold, or copper.

115. The device of any of the preceding Clauses, wherein the electrodes each comprise a coil, band, cap, or tube.

116. The device of any of the preceding Clauses, wherein the electrodes are coupled to the body in the distal portion.

117. The device of Claim 112, wherein the electrodes are electrically coupled to the body.

118. The device of any of the preceding Clauses, wherein the body comprises a plurality of struts forming a plurality of cells, and wherein at least one of the electrodes is coupled to one of the struts.

119. The device of any of the preceding Clauses, wherein the body comprises a plurality of struts forming a plurality of cells, and wherein at least one of the electrodes is coupled to a projection extending from one of the struts.

120. The device of any of the preceding Clauses, wherein the body comprises an electrically conductive material.

121. The device of any of the preceding Clauses, wherein the body is in electrical communication with the electrodes.

122. The device of any of the preceding Clauses, wherein the conductive leads are electrically insulated along at least a portion their respective lengths.

123. The device of any of the preceding Clauses, wherein the plurality of electrically conductive leads are bundled together along at least a portion of their respective lengths.

124. The device of any of the preceding Clauses, wherein a first set of the plurality of electrodes are configured to serve as delivery electrodes, and wherein a second set of the plurality of electrodes are configured to serve as return electrodes.

125. The device of any of the preceding Clauses, wherein the delivery electrodes are disposed within a working length of the body, and wherein the return electrodes are disposed within a non-working length of the body.

126. The device of any of the preceding Clauses, wherein the plurality of electrodes are configured to serve as delivery electrodes, the device further comprising a return electrode configured to be coupled to the current source.

127. The device of any of the preceding Clauses, wherein the plurality of electrodes are configured to serve as delivery electrodes, the device further comprising:
- a return electrode; and
- an electrically conductive return lead having a distal portion electrically coupled to the return electrode and a proximal portion configured to be electrically coupled to the current source.

128. The device of any of the preceding Clauses, wherein the return electrode comprises a needle or grounding pad.

129. The device of any of the preceding Clauses, wherein the return electrode comprises an exposed conductive member disposed adjacent a proximal portion of the body.

130. The device of any of the preceding Clauses, wherein the exposed conductive member is not carried by the body.

131. The device of any of the preceding Clauses, wherein the return electrode comprises a radiopaque marker coupled to the body and comprising an electrically conductive material.

132. The device of any of the preceding Clauses, wherein the delivery electrodes are disposed within a working length of the body, and wherein the return electrode is disposed within a non-working length of the body.

133. The device of any of the preceding Clauses, wherein the delivery electrodes and the return electrode are each disposed within a working length of the body.

134. The device of any of the preceding Clauses, wherein the body comprises a stent retriever.

135. The device of any of the preceding Clauses, wherein a portion of the body is coated with a conductive material.

136. The device of any of the preceding Clauses, wherein a portion of the body is coated with a non-conductive material.

137. A medical device comprising:
- an interventional element comprising a body that is expandable from a first configuration to a second configuration, the body having a working length;
- a shaft coupled to a proximal end of the body and extending longitudinally therefrom;
- at least one electrode located within the working length and configured for connection to a current source, such that, when the at least one electrode is energized, an electrical charge density around the body is greatest in the working length.

138. The device of any of the preceding Clauses, wherein the at least one electrode is electrically coupled to the body.

139. The device of any of the preceding Clauses, wherein the at least one electrode comprises a radiopaque element coupled to the body and comprising an electrically conductive material.

140. The device of any of the preceding Clauses, wherein the body comprises a plurality of struts forming a plurality of cells, and wherein the at least one electrode is coupled to one of the struts.

141. The device of any of the preceding Clauses, wherein the body comprises a plurality of struts forming a plurality of cells, and wherein at least one of the electrodes is coupled to a projection extending from one of the struts.

142. The device of any of the preceding Clauses, wherein the at least one electrode comprises a delivery electrode, the device further comprising at least one return electrode.

143. The device of any of the preceding Clauses, wherein the at least one return electrode is disposed within a non-working length of the body.

144. The device of any of the preceding Clauses, wherein the at least one return electrode is electrically insulated from the body.

145. The device of any of the preceding Clauses, wherein the return electrode comprises a radiopaque element coupled to the body and comprising an electrically conductive material.

146. The device of any of the preceding Clauses, wherein the interventional element comprises a stent retriever.

147. A method, comprising:
- advancing a thrombectomy device through a catheter to a target site in the body, the thrombectomy device comprising:
  - an expandable member having a working length and a non-working length;
  - one or more delivery electrodes coupled to the expandable member within the working length;
- supplying electrical current to the delivery electrode(s) such that a charge density is greater in the working length of the expandable member than along the non-working length of the expandable member.

148. The method of any of the preceding Clauses, wherein supplying current causes hydrogen gas to form at the target site.

149. The method of any of the preceding Clauses, wherein supplying electrical current to the delivery electrode(s) causes current to pass to the thrombectomy device.

150. The method of any of the preceding Clauses, wherein the thrombectomy device comprises an electrically conductive material.

151. The method of any of the preceding Clauses, wherein the thrombectomy device further comprises a plurality of delivery electrodes coupled to the expandable member, the method further comprising supplying electrical current to the plurality of delivery electrodes.

152. The method of any of the preceding Clauses, wherein the delivery electrode is coupled to a projection extending from a strut of the expandable member.

153. The method of any of the preceding Clauses, wherein the delivery electrode is coupled to a distally extending tip of the expandable member.

154. The method of any of the preceding Clauses, wherein the delivery electrode comprises at least one of: a coil or a band.

155. The method of any of the preceding Clauses, wherein supplying current produces a positive charge along at least a portion of the expandable member.

156. The method of any of the preceding Clauses, wherein a proximal end of the working length is distal of a proximal end of the expandable member and a distal end of the working length is proximal of a distal end of the expandable member.

157. The method of any of the preceding Clauses, wherein supplying electrical current includes delivering a direct current to the delivery electrode.

158. The method of any of the preceding Clauses, wherein supplying electrical current includes delivering a pulsatile current to the delivery electrode.

159. The method of any of the preceding Clauses, wherein supplying electrical current includes delivering a current to the delivery electrode, the current having an amplitude of between about 0.5 mA and about 5 mA.

160. The method of any of the preceding Clauses, wherein supplying electrical current includes delivering a current to the delivery electrode, the current having an amplitude of about 2 mA.

161. The method of any of the preceding Clauses, wherein the thrombectomy device comprises a stent retriever.

162. The method of any of the preceding Clauses, wherein the thrombectomy device is a laser-cut stent or a mesh.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.).

I. OVERVIEW OF ELECTRICALLY ENHANCED TREATMENT SYSTEMS

Figure 1A:
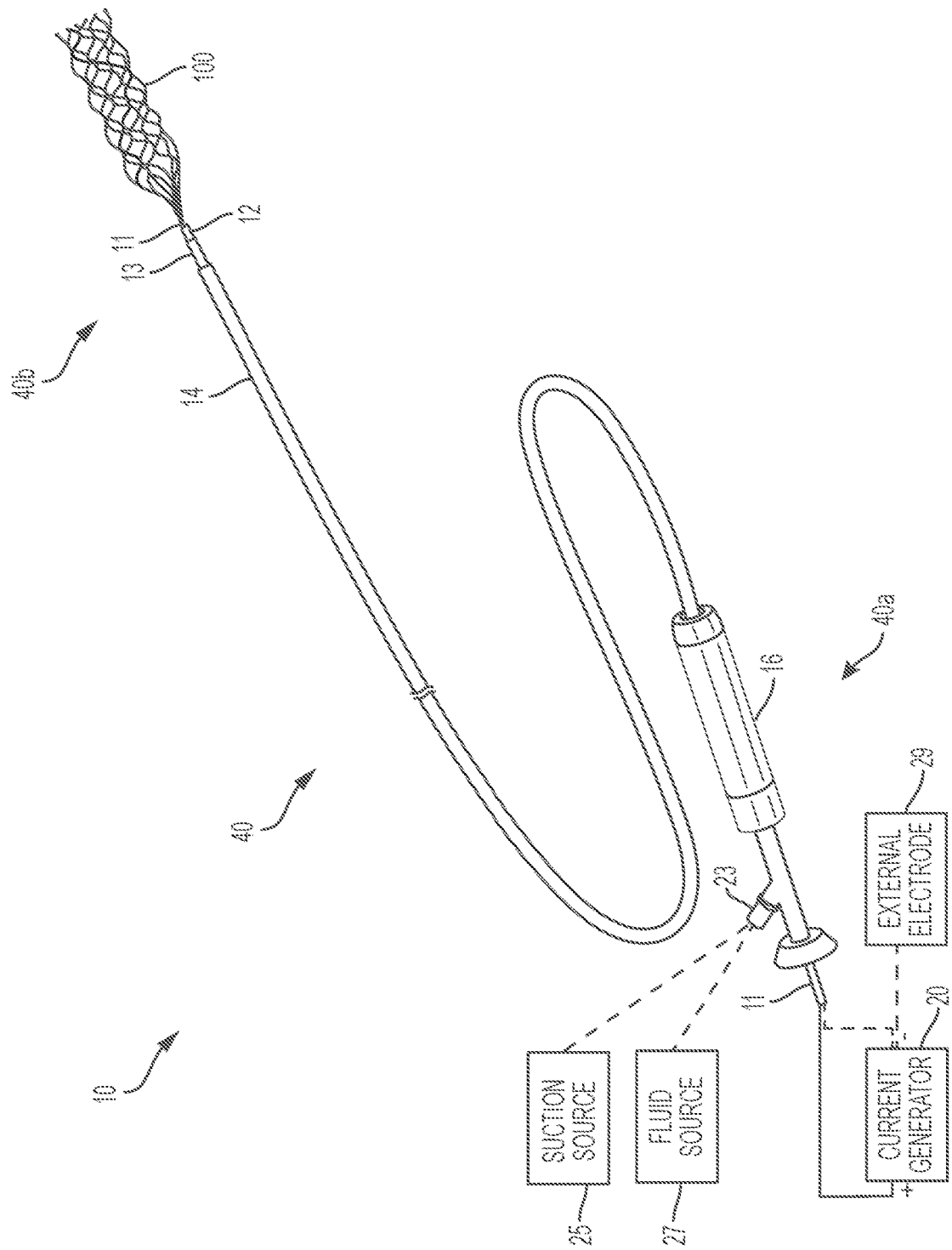
FIG. 1A shows a perspective view of an electrically enhanced treatment system for retrieving material from a body lumen, in accordance with one or more embodiments of the present technology.

FIG. 1A illustrates a view of an electrically enhanced treatment system 10 according to one or more embodiments of the present technology. As shown in FIG. 1A, the treatment system 10 can include a current generator 20 and a treatment device 40 having a proximal portion 40a configured to be coupled to the current generator 20 and a distal portion 40b configured to be intravascularly positioned within a blood vessel (such as an intracranial blood vessel) at a treatment site at or proximate a thrombus. The treatment device 40 includes an interventional element 100 at the distal portion 10b, a handle 16 at the proximal portion 10a, and a plurality of elongated shafts or members extending therebetween. For example, in some embodiments, such as that shown in FIG. 1A, the treatment device 40 includes a first catheter 14 (such as a balloon guide catheter), a second catheter 13 (such as a distal access catheter or aspiration catheter) configured to be slidably disposed within a lumen of the first catheter 14, a third catheter 12 (such as a microcatheter) configured to be slidably disposed within a lumen of the second catheter 13, and a core member 11 configured to be slidably disposed within a lumen of the third catheter 12. In some embodiments, the treatment device 40 does not include the second catheter 13. The first catheter 14 can be coupled to the handle 16, which provides proximal access to the core member 11 that engages the interventional element 100 at a distal end thereof. The current generator 20 may be coupled to a proximal portion of one or more leads (not shown) to deliver electrical current to the interventional element 100 and thereby provide an electrically charged environment at the distal portion 40b of the treatment device 40, as described in more detail below.

In some embodiments, the treatment system 10 includes a suction source 25 (e.g., a syringe, a pump, etc.) configured to be fluidically coupled (e.g., via a connector 23) to a proximal portion of one or more of the first catheter 14, the second catheter 13, and/or the third catheter 12 to apply negative pressure therethrough. In some embodiments, the treatment system 10 includes a fluid source 27 (e.g., a fluid reservoir, a syringe, pump, etc.) configured to be fluidically coupled (e.g., via the connector 23) to a proximal portion of one or more of the first catheter 14, the second catheter 13, and/or the third catheter 12 to supply fluid (e.g., saline, contrast agents, a drug such as a thrombolytic agent, etc.) to the treatment site.

According to some embodiments, the catheters 12, 13, and 14 can each be formed as a generally tubular member extending along and about a central axis. According to some embodiments, the third catheter 12 is generally constructed to track over a conventional guidewire in the cervical anatomy and into the cerebral vessels associated with the brain and may also be chosen according to several standard designs that are generally available. Accordingly, the third catheter 12 can have a length that is at least 125 cm long, and more particularly may be between about 125 cm and about 175 cm long. Other designs and dimensions are contemplated.

The second catheter 13 can be sized and configured to slidably receive the third catheter 12 therethrough. As noted above, the second catheter 13 can be coupled at a proximal portion to a suction source 25 (FIG. 1A) such as a pump or syringe in order to supply negative pressure to a treatment site. The first catheter 14 can be sized and configured to slidably receive both the second catheter 13 and the third catheter 12 therethrough. In some embodiments, the first catheter 14 is a balloonguide catheter having an inflatable balloon or other expandable member surrounding the catheter shaft at or near its distal end. As described in more detail below with respect to FIGS. 17A-17D, in operation the first catheter 14 can first be advanced through a vessel and then its balloon can be expanded to anchor the first catheter 14 in place and/or arrest blood flow from areas proximal of the balloon, e.g. to enhance the effectiveness of aspiration performed via the first catheter 14 and/or other catheter(s). Next, the second catheter 13 can be advanced through the first catheter 14 until its distal end extends distally beyond the distal end of the first catheter 14. The second catheter 13 can be positioned such that its distal end is adjacent a treatment site (e.g., a site of a blood clot within the vessel). The third catheter 12 may then be advanced through the second catheter 13 until its distal end extends distally beyond the distal end of the second catheter 13. The interventional element 100 may then be advanced through the third catheter 12 for delivery to the treatment site.

According to some embodiments, the bodies of the catheters 12, 13, and 14 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

Figure 1B:
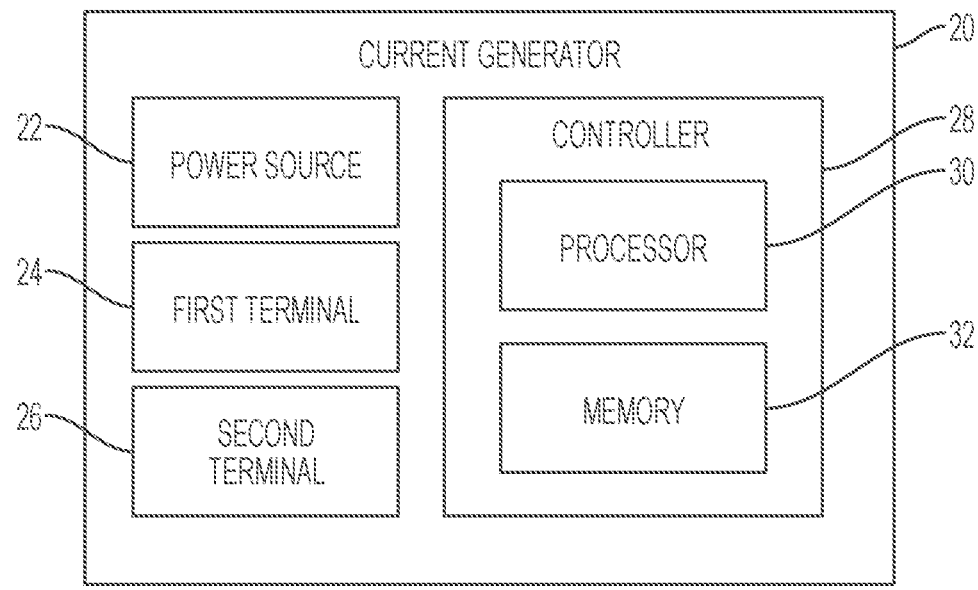
FIGS. 1B and 1C are schematic views of different embodiments of the current generator illustrated in FIG. 1A.
Figure 1C:
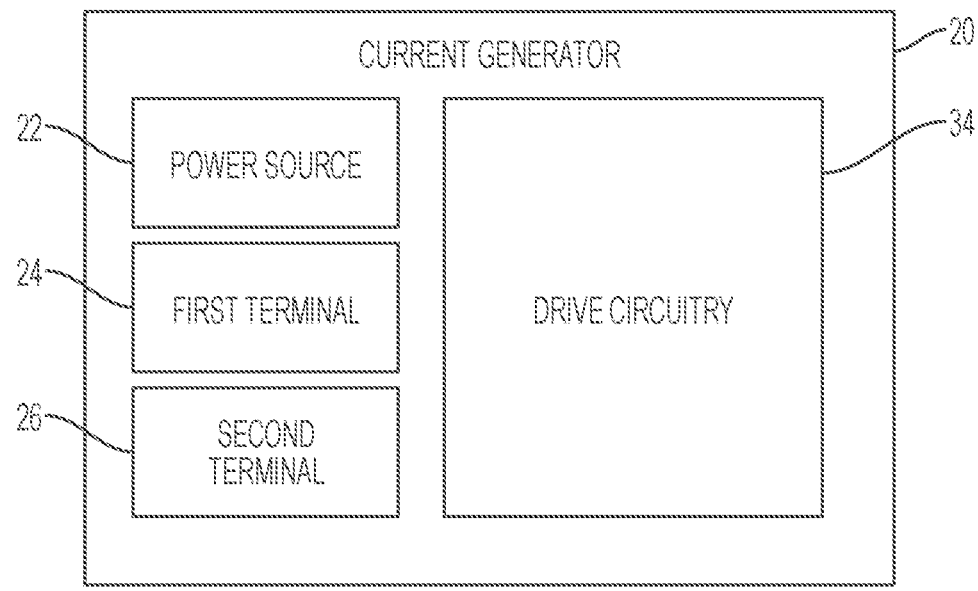

According to some embodiments, the current generator 20 can include an electrical generator configured to output medically useful electric current. FIGS. 1B and 1C are schematic views of different embodiments of the current generator 20. With reference to FIG. 1B, the current generator 20 can include a power source 22, a first terminal 24, a second terminal 26, and a controller 28. The controller 28 includes a processor 30 coupled to a memory 32 that stores instructions (e.g., in the form of software, code or program instructions executable by the processor or controller) for causing the power source 22 to deliver electric current according to certain parameters provided by the software, code, etc. The power source 22 of the current generator 20 may include a direct current power supply, an alternating current power supply, and/or a power supply switchable between a direct current and an alternating current. The current generator 20 can include a suitable controller that can be used to control various parameters of the energy output by the power source or generator, such as intensity, amplitude, duration, frequency, duty cycle, and polarity. For example, the current generator 20 can provide a voltage of about 2 volts to about 28 volts and a current of about 0.5 mA to about 20 mA.

FIG. 1C illustrates another embodiment of the current generator 20, in which the controller 28 of FIG. 1B is replaced with drive circuitry 34. In this embodiment, the current generator 20 can include hardwired circuit elements to provide the desired waveform delivery rather than a software-based generator of FIG. 1B. The drive circuitry 34 can include, for example, analog circuit elements (e.g., resistors, diodes, switches, etc.) that are configured to cause the power source 22 to deliver electric current via the first and second terminals 24, 26 according to the desired parameters. For example, the drive circuitry 34 can be configured to cause the power source 22 to deliver periodic waveforms via the first and second terminals 24, 26. Particular parameters of the energy provided by the current generator 20 are described in more detail below with respect to FIGS. 18A-18E.

In some embodiments, one or more electrodes can be carried by, coupled to or mounted on the interventional element 100 (or the electrodes can comprise conductive elements or surfaces other than radiopaque elements/markers (if any)). The electrodes can optionally take the form of radiopaque elements or markers affixed to a portion of the interventional element 100, and can be arranged so as to provide and/or improve electrical charge distribution over the surface of the interventional element 100 during treatment. Current can be delivered to the electrodes over a plurality of corresponding electrical leads extending between the current generator 20 and the electrodes affixed to the interventional element 100. The electrodes can comprise delivery electrodes as well as one or more return electrodes, which can likewise be coupled to or formed on the interventional element 100, or may be positioned elsewhere (e.g., as an external electrode 29, or otherwise, as will be explained in greater detail below). When the interventional element 100 is placed in the presence of blood (or thrombus, and/or any other electrolytic medium which may be present, such as saline) and voltage is applied at the terminals of the current generator 20, current flows from the generator along the leads to the delivery electrodes (and, optionally, to the interventional element 100 itself), through the blood (and/or other medium), and to the return electrode(s), thereby positively charging at least a portion of the interventional element 100 and promoting clot adhesion.

Figure 2:
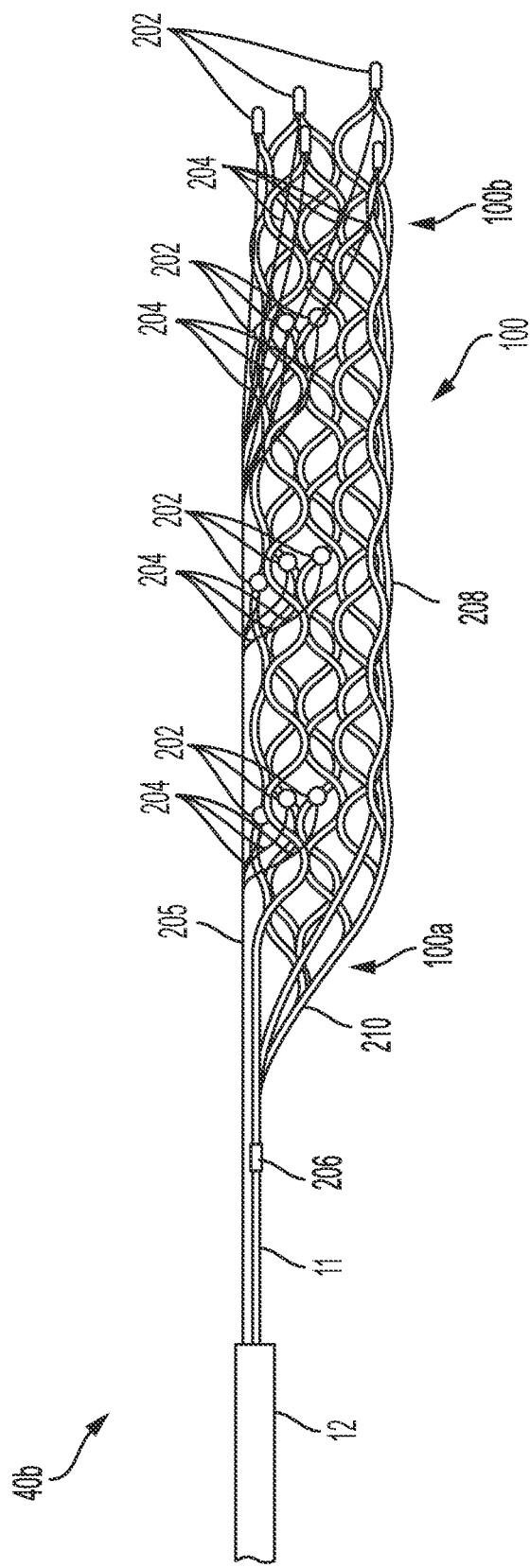
FIG. 2 is a side schematic view of a distal portion of the treatment system of FIG. 1A.

FIG. 2 is a side schematic view of the distal portion 40b of the treatment device 40 shown in FIG. 1A. As illustrated, the interventional element 100 can include a plurality of electrodes 202 disposed thereon. The electrodes 202 can take the form of electrically conductive members or surfaces coupled to or incorporated in the body of the interventional element 100 at various locations. For example, each electrode 202 can be coupled to a strut, to a projection extending away from a strut, to a distally extending tip, or any other suitable portion of the interventional element 100. In some embodiments, the electrodes 202 can be radiopaque so as to be visible under fluoroscopy. (Generally, "radiopaque" as used herein refers to an element or component which is more visible under fluoroscopy than an adjacent portion of the interventional element 100 itself.) In such configurations, the electrodes 202 can function as both radiopaque markers and electrodes. According to some embodiments, some or all of the electrodes 202 can take the form of coils, tubes, bands, plates, traces, or any other suitable structure that is electrically conductive, or both electrically conductive and radiopaque. Exemplary materials for the electrodes include copper, stainless steel, nitinol, platinum, gold, iridium, tantalum, alloys thereof, or any other suitable materials that are electrically conductive, or both electrically conductive and radiopaque. In some embodiments, the electrodes 202 are not radiopaque, and separate radiopaque markers may or may not be used in conjunction with such non-radiopaque electrodes 202.

The electrodes 202 can each be coupled to a respective electrical lead 204 that may extend alongside the core member 11, and/or be coupled to, wound around or incorporated into the core member 11. When the thrombectomy device is in use with the catheter 12, therefore, the lead(s) may extend through the lumen of the catheter 12. The electrical leads 204 can be bundled together or otherwise grouped together in a lead bundle assembly 205 that extends proximally adjacent the core member 11 through the catheter 12. The bundle assembly 205 can couple at a proximal end portion to the current generator (e.g., current generator 20; FIG. 1A), with each individual lead 204 being electrically coupled to the current generator to carry current to a respective electrode 202. Although FIG. 2 illustrates a separate electrical lead 204 coupled to each individual electrode 202, in some embodiments any subset of electrodes 202 may share electrical connection via one or more leads 204. For example, a lead may extend between two electrodes 202, thereby placing those two electrodes in electrical communication with one another as well as the generator or other current source, when coupled thereto.

In some embodiments, a first subset of the electrodes 202 can be electrically coupled to the positive terminal of the current generator 20 via their respective leads 204, and accordingly serve as delivery electrodes. Meanwhile, a second subset of the electrodes 202 can be electrically coupled to the negative terminal of the current generator 20 via their respective leads 204 and accordingly serve as return electrodes. In some embodiments, some or all of the delivery electrodes 202 can be in electrical communication with the body of the interventional element 100 (or electrically insulated therefrom), which may itself be electrically conductive. When some or all of the delivery electrodes 202 are in electrical communication with the (electrically conductive) body of the interventional element 100, the positive/delivery lead 204 (e.g., a single such lead) can be electrically coupled to the body of the interventional element 100, e.g., at or near the proximal end thereof, and thereby in electrical communication with some or all of the delivery electrodes 202. As such, current carried by the delivery electrodes 202 can flow into the interventional element 100, thereby generating a positive charge along at least a portion of the interventional element 100 (as well as any delivery electrodes 202 coupled to the body of the interventional element; in some embodiments, separate delivery electrodes 202 can be omitted and the body of the interventional element (or exposed portion(s) thereof) can serve as the delivery electrode(s)). In some embodiments, one or more regions of the interventional element 100 can be coated with an insulative material such that current carried from the delivery electrodes 202 to the interventional element 100 will not be carried by the surface of the interventional element 100 in the coated regions. As a result, the distribution of charge over the surface or along the length of the interventional element 100 can be located in the region(s) of the interventional element 100 that are not coated with an insulative material.

In some embodiments, the return electrodes 202 can be carried by the interventional element 100 but be electrically insulated from the body of the interventional element 100. For example, the return electrodes 202 can be mounted over a portion of the interventional element 100 with an electrically insulating material disposed therebetween such that current carried by a return electrode 202 does not pass to the body of the interventional element 100, but instead passes through the corresponding lead 204 coupled to the return electrode 202. In some embodiments, the return electrodes 202 can be in electrical communication with at least a portion of the interventional element 100.

During operation, the treatment system 10 can provide an electrical circuit in which current flows from the positive terminal of the current generator 20, distally through the delivery leads 204 to delivery electrodes 202 and (optionally) to the interventional element 100. Current then passes from the surface of the interventional element 100 (when suitably configured) and to the surrounding media (e.g., blood, tissue, thrombus, etc.) before returning via the return electrodes 202 carried by the interventional element 100, proximally through the return leads 204, and to the negative terminal of the current generator.

Instead of or in addition to the return electrodes 202 carried by the interventional element 100, the return electrode(s) can assume a variety of different configurations. For example, in some embodiments, the return electrode is an external electrode 29 (FIG. 1A), such as a needle or grounding pad that is applied to a patient's skin. The needle or grounding pad can be coupled via one or more leads to the current generator 20 to complete the electrical circuit. In some embodiments, the return electrode is carried by a surrounding catheter (e.g., third catheter 12, second catheter 13, and/or first catheter 14). In some embodiments, the return electrode can be an insulated guide wire having an exposed, electrically conductive portion at its distal end, or an exposed, electrically conductive portion of the core member 11 near its distal end.

II. SELECT EMBODIMENTS OF INTERVENTIONAL ELEMENTS FOR USE WITH THE TREATMENT SYSTEMS DISCLOSED HEREIN

Referring still to FIG. 2, in some embodiments the interventional element 100 can be a metallic or electrically conductive thrombectomy device. For example, the interventional element 100 can include or be made of stainless steel, nitinol, cobalt-chromium, platinum, tantalum, alloys thereof, or any other suitable material. The interventional element 100 can have a low-profile, constrained or compressed configuration (not shown) for intravascular delivery to the treatment site within the third catheter 12, and an expanded configuration for securing and/or engaging clot material and/or for restoring blood flow at the treatment site. In some embodiments, the interventional element 100 is a mesh structure (e.g., a braid, a stent, etc.) formed of a superelastic material (e.g., Nitinol) or other resilient or self-expanding material configured to self-expand when released from the third catheter 12. The interventional element 100 has a proximal portion 100a that may be coupled to the core member 11 and a distal portion 100b. The interventional element 100 further includes an open cell framework or body 208 and a coupling region 210 extending proximally from the body 208. In some embodiments, the body 208 of the interventional element 100 can be generally tubular (e.g., cylindrical), and the proximal portion 100a of the interventional element 100 can be tapered proximally within the coupling region 210.

In various embodiments, the interventional element 100 can take any number of forms, for example a removal device, a thrombectomy device, or other suitable medical device. For example, in some embodiments the interventional element 100 may be a stent and/or stent retriever, such as Medtronic's Solitaire™ Revascularization Device, Stryker Neurovascular's Trevo® ProVue™ Stentriever, or other suitable devices. In some embodiments, the interventional element 100 may be a coiled wire, a weave, and/or a braid formed of a plurality of braided filaments. Examples of suitable interventional elements 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The core member 11 can comprise a shaft, e.g., having sufficient column strength and tensile strength to facilitate moving the thrombectomy device through a catheter. The core member 11 can comprise a wire, which can if desired be tapered to a take on a smaller diameter as it extends distally. Such a taper can be implemented as a gradual or continuous taper, or in a plurality of discrete tapered sections separated by constant-diameter sections. The core member 11 can alternatively comprise a tube, such as a hypotube, and the tube/hypotube can be laser-cut with a spiral or slotted pattern, or otherwise, to impart added flexibility where desired. The core member can also comprise a combination of wires, tubes, braided shafts etc.

Figure 3A:
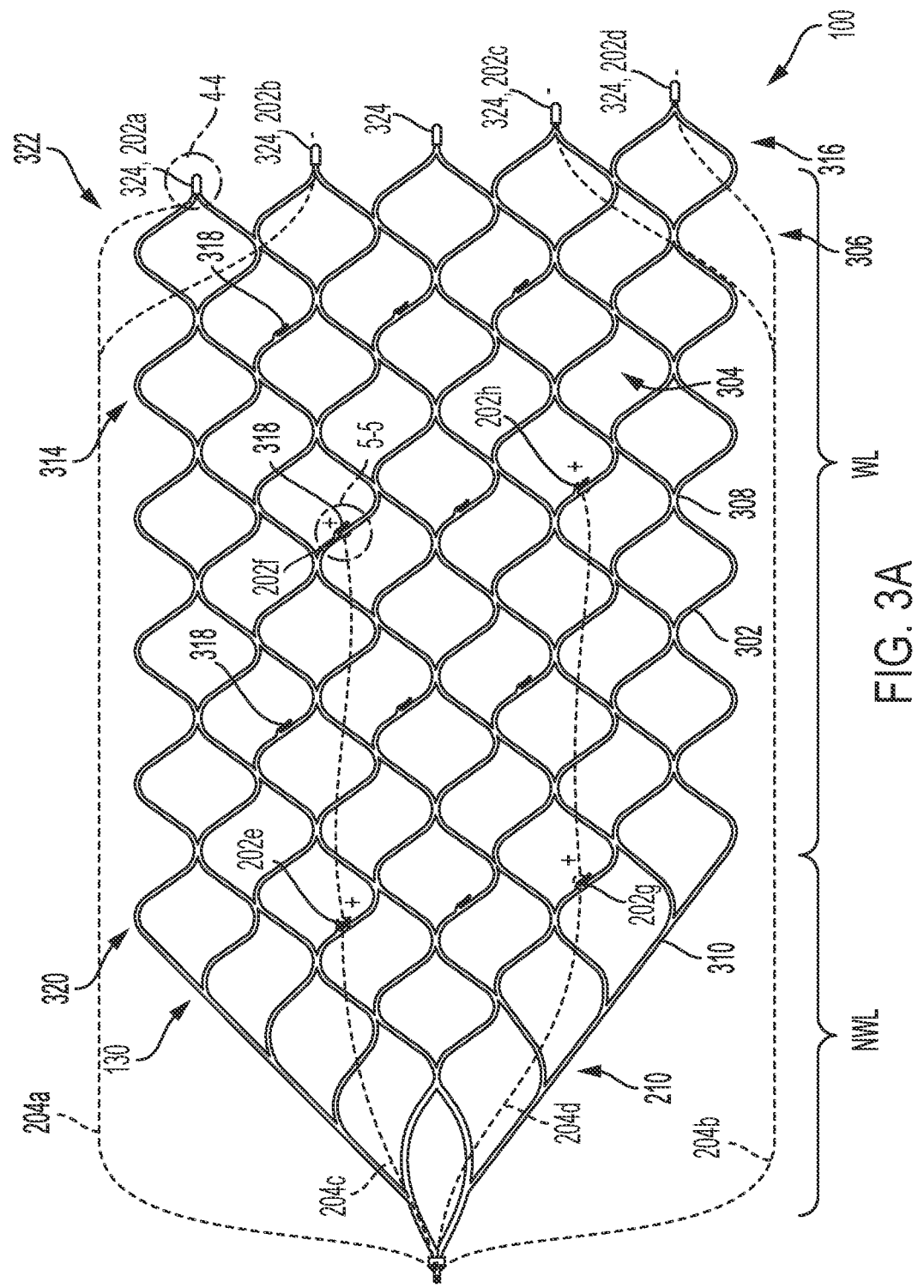
FIG. 3A illustrates an interventional element carrying a plurality of electrodes in an unrolled state in accordance with embodiments of the present technology.

FIG. 3A illustrates an example interventional element 100 carrying a plurality of electrodes 202 thereon in a "flat" view for ease of understanding. The interventional element 100 illustrated in FIG. 3A includes a working length WL and a non-working length NWL located proximal of the working length WL. As illustrated in FIG. 3A, for example, the non-working length NWL is disposed between the working length WL and the connection to the core member 11. In some embodiments, the interventional element 100 can comprise a frame or body having a plurality of struts 302 and a plurality of cells 304 located between the struts, forming a mesh. Groups of longitudinally and serially interconnected struts 302 can form undulating members 306 that extend in a generally longitudinal direction. The struts 302 can be connected to each other by joints 308. While the struts are shown having a particular undulating or sinuous configurations, in some embodiments the struts can have other configurations. In the rolled configuration, the frame of the interventional element 100 can have a generally tubular or generally cylindrical shape in some embodiments, while in others the frame can have a shape that is neither tubular nor cylindrical.

The working length WL of the interventional element illustrated in FIG. 3A comprises some of the cells 304. In embodiments wherein the interventional element 100 comprises cells, the cells 304 in the working length and the portion of the interventional element that form them can be sized and shaped such that they penetrate into a thrombus, capture a thrombus, or both upon expansion of the working length into a thrombus. In some embodiments, the portion of the interventional element 100 in the working length can capture the thrombus with the individual cells 304 and/or with an exterior, or radial exterior, of the expanded interventional element 100. Additionally or alternatively, in some embodiments, the portion of the interventional element 100 in the working length may contact, interlock, capture or engage with a portion of the thrombus with individual cells 304 and/or an interior, or radial interior, of the expanded interventional element 100.

As illustrated in FIG. 3A, for example, the non-working length NWL can comprise a tapered proximal portion 310 of the interventional element 100. The proximal portion 310 of the interventional element 100 can be tapered toward a proximal end of the interventional element 100. In some embodiments, the taper of the proximal, non-working portion 310 can advantageously facilitate retraction and repositioning of the treatment device 40 and interventional element 100. For example, in some embodiments, the non-working length NWL facilitates a retraction of the interventional element 100 into the catheter 12.

The interventional element 100 can comprise a first edge 314 and a second edge 316. The first edge 314 and second edge 316 can be formed, for example, from cutting a sheet or a tube. While the first and second edges are shown as having an undulating, or sinuous configuration, in some embodiments the first and second edges can have a straight, or linear configuration, or other configuration. In some embodiments, the edges 314, 316 can be curved, straight, or a combination thereof along the tapered proximal portion 310.

FIG. 3A also illustrates a plurality of projections 318, on which an electrode 202 or radiopaque marker can be mounted. Each projection 318 can be attached to a portion of the interventional element 100 that may contact thrombus during use of the interventional element. In some embodiments, the projections 318 can be attached to portions of the interventional element 100 in the working length WL. In embodiments wherein the interventional element comprises struts 302, the projection(s) 318 can be attached to strut(s) 302. The projection 318 can be disposed within a cell 304, if present, or on another surface of the interventional element 100. In some embodiments, a plurality of projections 318 can be attached respectively to a plurality of struts 302. In some embodiments, some or all of the projections 318 can each be attached to and/or at only a single strut 302. In some embodiments, the projection 318 can be attached to and/or at a joint 308. In some embodiments, the projections 318 can be separated from all other projections 318 by a distance, for example at least 2 mm or at least 3 mm, in a fully expanded configuration of the interventional element 100. In some embodiments, the projections 318 can be separated from all other projections 318 by one cell width or one strut length (e.g., an entire length of a strut separates the adjacent projections). One or more projections 318 can be located at some or all of a proximal end 320 of the working length WL, a distal end 322 of the working length WL, or an intermediate area of the working length WL between the proximal end 322 and the distal end 322. The working length WL can extend continuously or intermittently between the proximal end 320 and the distal end 322.

In some embodiments, the interventional element 100 can comprise one or more distally extending tips 324 extending from a distal end of the interventional element 100. For example, the device illustrated in FIG. 3A is shown comprising five elongate, distally extending tips 324 extending from a distal end of the interventional element 100. In some embodiments wherein the interventional element comprises struts, these distal tips 324 can extend from a distalmost row of struts, for example as illustrated in FIG. 3A. In some embodiments, one or more electrodes 202 and/or one or more radiopaque markers can be attached to the distal tips 324, if present. In some embodiments wherein one or more markers or electrodes are attached to the distal tips, the marker(s) or electrodes 202 on the distal tips 324 can be positioned at the distal end 322 of the working length WL, for example as illustrated in FIG. 3A.

As shown in FIG. 3A, a plurality of electrodes 202 can be coupled to the body of the interventional element 100. Each of the electrodes 202 can be coupled to an electrical lead 204 which in turn can be coupled to the current generator (e.g., current generator 20; FIG. 1A), or other suitable current source. Some or all of the electrodes 202 can take the form of electrically conductive elements affixed to portions of the interventional element 100. For example, some or all of the electrodes 202 can be metallic, electrically conductive, and optionally radiopaque (e.g., including copper, platinum, gold, alloys thereof, or any other suitable material). In some embodiments, some or all of the electrodes 202 take the form of coils, bands, tubes, caps, or any other suitable structural element that can be mounted to the interventional element 100 and placed in electrical communication with a corresponding lead 204. In some embodiments, the electrodes 202 can be soldered, welded, crimped, adhesively mounted or otherwise adhered to the interventional element 100. As described in more detail elsewhere herein, in some embodiments at least some (or all) of the electrodes 202 can be in electrical communication with the body of the interventional element 100, which may itself comprise an electrically conductive material (e.g., nitinol, stainless steel, etc.), such that current flows through the electrodes 202 and into the interventional element 100. In some embodiments, at least some (or all) of the electrodes 202 can be carried by the interventional element 100 yet remain electrically insulated from the interventional element, for example by disposing an electrically insulative material between the electrode 202 and the body of the interventional element 100. In such configurations, current flowing through such an insulated electrode 202 does not pass to the underlying interventional element 100 on which the electrode 202 is mounted or otherwise coupled.

As noted, each of the electrodes 202 can be in electrical communication with an electrical lead 204. Some or all of the leads 204 can take the form of an elongate conductive member that is insulated along some or all of its length. For example, some or all of the leads 204 can take the form of conductive wires having an insulative coating along at least a portion of their lengths. Some or all of the leads can comprise other conductive structures such as traces (e.g. printed or deposited traces), tubes, buses, bars, coils, doped polymeric strands, etc. As one example, a lead 204 can take the form of a metallic wire (e.g., nitinol, copper, stainless steel, etc.). In some embodiments, the wire can have a thickness or diameter of between about 0.005 mm to about 0.125 mm, or between about 0.005 mm to about 0.05 mm (e.g., a 58 AWG wire). Such a wire may have a substantially uniform thickness along its length or may be tapered distally or proximally. The leads 204 can have a length of greater than about 125 cm, about 150 cm, about 175 cm, or about 200 cm. An insulative coating surrounding the wire can include any suitable electrically insulative material (e.g., polyimide, Parylene, PTFE, etc.). The leads 204 can be soldered, welded, or otherwise adhered to their respective electrodes 202. Although some of the leads 204 are shown schematically in FIG. 3A as extending outside the body or inner lumen of the interventional element 100, in various embodiments some or all of the leads 204 may be routed along a radially inward or radially outward surface of the interventional element 100, or optionally may be routed through one or more cells 304, for example in an undulating fashion such that a lead 204 is woven through alternating cells 304 in an over-under pattern. In some embodiments, a lead 204 may be wound (once, or multiple times) around each of one or more struts 302 positioned proximal of the electrode(s) coupled to the lead to more securely fasten the lead 204 to the body of the interventional element 100.

The individual leads 204a-d can be coupled together at a proximal junction and meet in a lead bundle assembly (not shown) as described in more detail elsewhere here (e.g., with respect to FIGS. 14A-16B). Whether arranged in a lead bundle assembly or as discrete and separate elements, the leads 204a-d may extend proximally through a surrounding catheter (and/or be coupled to or integrated into the core member 11) to be electrically coupled to the current generator or other current source.

Figure 4:
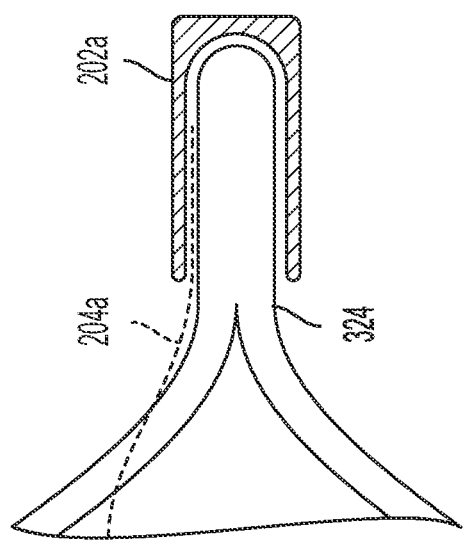
FIG. 4 is a detailed view of segment 4-4 shown in FIG. 3A.

In the illustrated embodiment of FIG. 3A, first and second electrodes 202a and 202b are coupled to distally extending tips 324, and the first and second electrodes 202a and 202b are electrically coupled to a first electrical lead 204a, which extends proximally along the length of the interventional element 100. A detailed view of the first electrode 202a mounted over a distally extending tip 324 is shown in FIG. 4. The electrode 202a can take the form of a coil, band, cap, or tube that fits over the distally extending tip 324. In various embodiments, the electrode 202a can extend around some or all of a circumference of the distally extending tip 324. In some embodiments, the electrode 202a can have a length of between about 0.5 and 2.0 mm, or about 0.85 mm. In some embodiments, the electrode 202a can have a width of between about 0.05 and 0.4 mm, or about 0.20 mm. The first lead 204a can be electrically coupled to the electrode 202a. For example, the first lead 204a can be soldered, welded, or otherwise adhered to and in electrical communication with the electrode 202a. In some embodiments, a distal end portion of the lead 204a extends into the space between the electrode 202a and the distally extending tip 324. According to some embodiments, the electrode 202a and/or the lead 204a may be in electrical communication with the material of the distally extending tip 324. In other embodiments, an insulative material may be disposed between the electrode 202a and the distally extending tip 324 (and/or an insulating material may be disposed between the lead 204a and the distally extending tip 324) such that current flowing through the electrode 202a and/or the lead 204a is inhibited from passing to the underlying distally extending tip 324 of the interventional element 100.

Referring back to FIG. 3A, third and fourth electrodes 202c and 202d can similarly take the form of conductive (and optionally radiopaque) elements coupled to distally extending tips 324. In the illustrated embodiment, the third and fourth electrodes 202c and 202d are electrically coupled to a second electrical lead 204b that extends proximally along the length of the interventional element 100.

Figure 5:
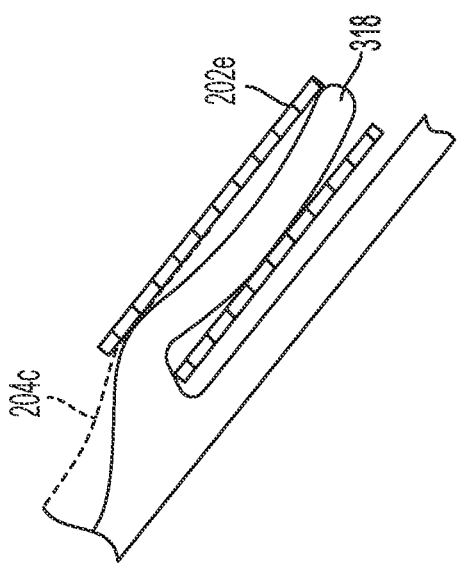
FIG. 5 is a detailed view of segment 5-5 shown in FIG. 3A.

With continued reference to FIG. 3A, fifth and sixth electrodes 202e and 202f take the form of conductive members mounted on projections 318 that extend away from (and/or alongside) struts 302 (and/or within cells 304) of the interventional element 100, and a third electrical lead 204c is electrically coupled to the fifth and sixth electrodes 202e and 202f. A detailed view of the fifth electrode 202e mounted over a projection 318 is shown in FIG. 5. The electrode 202e can take the form of a coil or band that fits over the projection 318. In various embodiments, the electrode 202e can extend around some or all of a circumference of the projection 318. In some embodiments, the electrode 202e can have a length of between about 0.5 mm and about 2 mm, for example about 0.80 mm. In some embodiments, the electrode 202e can have a width of between about 0.05 and 0.2 mm, or about 0.11 mm. The third lead 204*c* can be electrically coupled to the electrode 202*e*. For example, the lead 204*c* can be soldered, welded, or otherwise adhered to and in electrical communication with the electrode 202*e*. In some embodiments, a distal end portion of the lead 204*c* extends into the space between the electrode 202*e* and the projection 318. According to some embodiments, the electrode 202*e* and/or the lead 204*c* may be in electrical communication with the material of the projection 318. In other embodiments, an insulative material may be disposed between the electrode 202*e* and the projection 318 (and/or an insulating material may be disposed between the lead 204*c* and the projection 318) such that current flowing through the electrode 202*e* and/or the lead 204*c* is inhibited from passing to the underlying projection 318 of the interventional element 100.

Referring back to FIG. 3A, seventh and eighth electrodes 202*g* and 202*h* can similarly take the form of conductive (and optionally radiopaque) elements coupled to projections 318. In the illustrated embodiment, the seventh and eighth electrodes 202*g* and 202*h* are electrically coupled to a fourth electrical lead 204*d* that extends proximally along the length of the interventional element 100.

In the example shown in FIG. 3A, there are four discrete electrical leads 204 each coupled to two electrodes 202, for a total of eight addressable electrodes 202. This configuration is only exemplary; in other embodiments there may be fewer or more electrodes (e.g., 1, 2, 3, 4, 5, 6, 7, 9, 10, 11, 12, or more electrodes carried by the interventional element 100). Similarly, there may be fewer or more leads 204.

By selecting the positioning of the individual electrodes 202, the electrical charge distribution over the interventional element 100 can be tailored to achieve the desired results during treatment. For example, by coupling electrodes 202*e*, 202*f*, 202*g*, and 202*h* to the positive terminal of a current generator (e.g., by coupling leads 204*c* and 204*d* to the positive terminal of a current generator), these electrodes 202*e*, 202*f*, 202*g*, and 202*h* can deliver positive electrical charge to respective portions of the interventional element 100. As such, these may serve as delivery electrodes. If any of these electrodes are in electrical communication with the interventional element 100, this positive current may flow into the interventional element 100, thereby positively charging a greater portion of the surface of the interventional element 100. In some embodiments, a portion of the interventional element 100 can be coated with an electrically insulative material so as to selectively concentrate electrical charge in certain regions (e.g., within the working length WL). In accordance with some embodiments, some or all of the delivery electrodes 202*e*, 202*f*, 202*g*, and 202*h* are not in electrical communication with the interventional element 100 (e.g., due to the presence of an insulative material disposed between the delivery electrodes and their respective projections 318).

In some embodiments, an electrode 202 coupled to a projection 318 located at the proximal end 320 of the working length WL can be disposed within 5 mm, within 4 mm, within 3 mm, within 2 mm, or within 1 mm, proximally or distally, of the proximal end 320. In some embodiments, an electrode 202 coupled to a projection 318 located at the proximal end 320 can be disposed within the length of one cell or one strut, proximally or distally, of the proximal end 322.

In some embodiments, an electrode 202 coupled to a projection 318 located at the distal end 322 of the working length WL can be disposed within 5 mm, within 4 mm, within 3 mm, within 2 mm, or within 1 mm, proximally or distally, of the distal end 322. In some embodiments, an electrode coupled to a projection 318 located at the distal end 322 can be disposed within the length of one cell or one strut, proximally or distally, of the distal end 322.

In addition to electrode positioning, the charge distribution is affected by the configuration of the delivery electrodes (e.g., material, size, surface area), the delivery leads (e.g., material, cross-sectional size) and the amount of current delivered. For example, a decreased number or surface area of the electrodes results in increased charge density at the electrodes. If the charge density is too high, it may present health risks when used in the body. However, at certain thresholds of charge density, hydrogen gas can be generated at the electrodes 202 or on other portions of the interventional element 100. In some instances, hydrogen gas can be neuroprotective, and accordingly it can be advantageous to provide a selective high enough charge density to generate hydrogen gas within the patient's neurovasculature.

In the illustrated embodiment, the distally positioned electrodes 202*a*, 202*b*, 202*c*, and 202*d* are coupled to the negative terminal of a current generator (e.g., by coupling leads 204*a* and 204*b* to the negative terminal of a current generator) and accordingly these electrodes serve as return electrodes. In some embodiments, the return electrodes may be electrically insulated from the interventional element 100, for example by disposing an insulative material between the distally extending tips 324 and the respective electrodes 202*a*, 202*b*, 202*c*, and/or 202*d*.

In operation, an electrical circuit is provided in which current flows from the positive terminal of the current generator, distally through the delivery leads 204*c* and 204*d* to delivery electrodes 202*e*, 202*f*, 202*g*, and 202*h*, and to the interventional element 100 (if one or more of the delivery electrodes are in electrical communication with the interventional element 100). Current then passes from the surface of the interventional element 100 and/or from the delivery electrodes and to the surrounding media (e.g., blood, tissue, thrombus, etc.) before returning back to the return electrodes 202*a*, 202*b*, 202*c*, and 202*d*. The current then flows proximally through the return leads 204*a* and 204*b*, and back to the negative terminal of the current generator. Alternatively, the return electrode(s) can be provided elsewhere, for example via an external needle or grounding pad, via an insulated guidewire with an exposed distal portion or an exposed electrode portion of the core member 11, coupled to a distal portion of a catheter, etc. In such cases, the return electrode(s) may optionally be omitted from the interventional element 100.

In some embodiments, the non-working length NWL portion of the interventional element 100 can be coated with a non-conductive or insulative material (e.g., Parylene, PTFE, or other suitable non-conductive coating) such that the coated region is not in electrical contact with the surrounding media (e.g., blood). As a result, the current carried by the delivery electrodes 202 to the interventional element 100 is only exposed to the surrounding media along the working length WL portion of the interventional element 100. This can advantageously concentrate the electrically enhanced attachment effect along the working length WL of the interventional element 100, where it is most useful, and thereby combine both the mechanical interlocking provided by the working length WL and the electrical enhancement provided by the delivered electrical signal. In some embodiments, a distal region of the interventional element 100 (e.g. distal of the working length WL) may likewise be coated with a non-conductive material (e.g., Parylene, PTFE, or other suitable non-conductive coating), leaving only a central portion or the working length WL of the interventional element 100 having an exposed conductive surface.

In some embodiments, the proximal end of the working length can be at a proximalmost location where the interventional element forms a complete circumference. In some embodiments, the proximal end of the working length can be at a proximalmost location where the interventional element has its greatest transverse dimension in a fully expanded state. In some embodiments, the proximal end of the working length can be at a proximalmost location where the interventional element has a peak, crown, or crest in transverse dimension in a fully expanded state.

In some embodiments, the distal end of the working length can be at a distalmost location where the interventional element forms a complete circumference. In some embodiments, the distal end of the working length can be at a distalmost location where the interventional element has its greatest transverse dimension in a fully expanded state. In some embodiments, the distal end of the working length can be at a distalmost location where the interventional element has a peak, crown, or crest in transverse dimension in a fully expanded state.

In some embodiments, the interventional element 100 may include a conductive material positioned on some or all of its outer surface. The conductive material, for example, can be gold and/or another suitable conductor that has a conductivity greater than (or a resistivity less than) that of the material comprising the interventional element 100. The conductive material may be applied to the interventional element 100 via electrochemical deposition, sputtering, vapor deposition, dip-coating, and/or other suitable means. In some aspects of the present technology, a conductive material is disposed only on the working length WL portion of the interventional element 100, e.g., such that the proximal and distal end portions of the interventional element 100 are exposed or not covered in the conductive material. In such configurations, because the conductive material has a much lower resistance than the underlying material comprising the interventional element 100, current delivered to the interventional element 100 is concentrated along the working length WL portion. In several of such embodiments, the conductive material may be disposed on only a radially outwardly facing strut surface along the working length WL portion. In other embodiments, the conductive material may be disposed on all or a portion of the strut surface along all or a portion of the length of the interventional element 100.

In some embodiments, a first portion of the interventional element 100 is covered by a conductive material and a second portion of the interventional element 100 is covered by an insulative or dielectric material (e.g., Parylene). For example, in some embodiments a radially outwardly facing surface of the strut surface is covered by a conductive material while a radially inwardly facing surface of the strut surface is covered by an insulative material. In some embodiments, the working length WL portion of the interventional element 100 may be covered by a conductive material while the non-working length NWL portion is covered by an insulative material. In some embodiments, the conductive material may be disposed on all or a portion of the strut surface along all or a portion of the length of the interventional element 100, and the insulative material may be disposed on those portions of the strut surface and/or working length not covered by the conductive material.

Figure 3B:
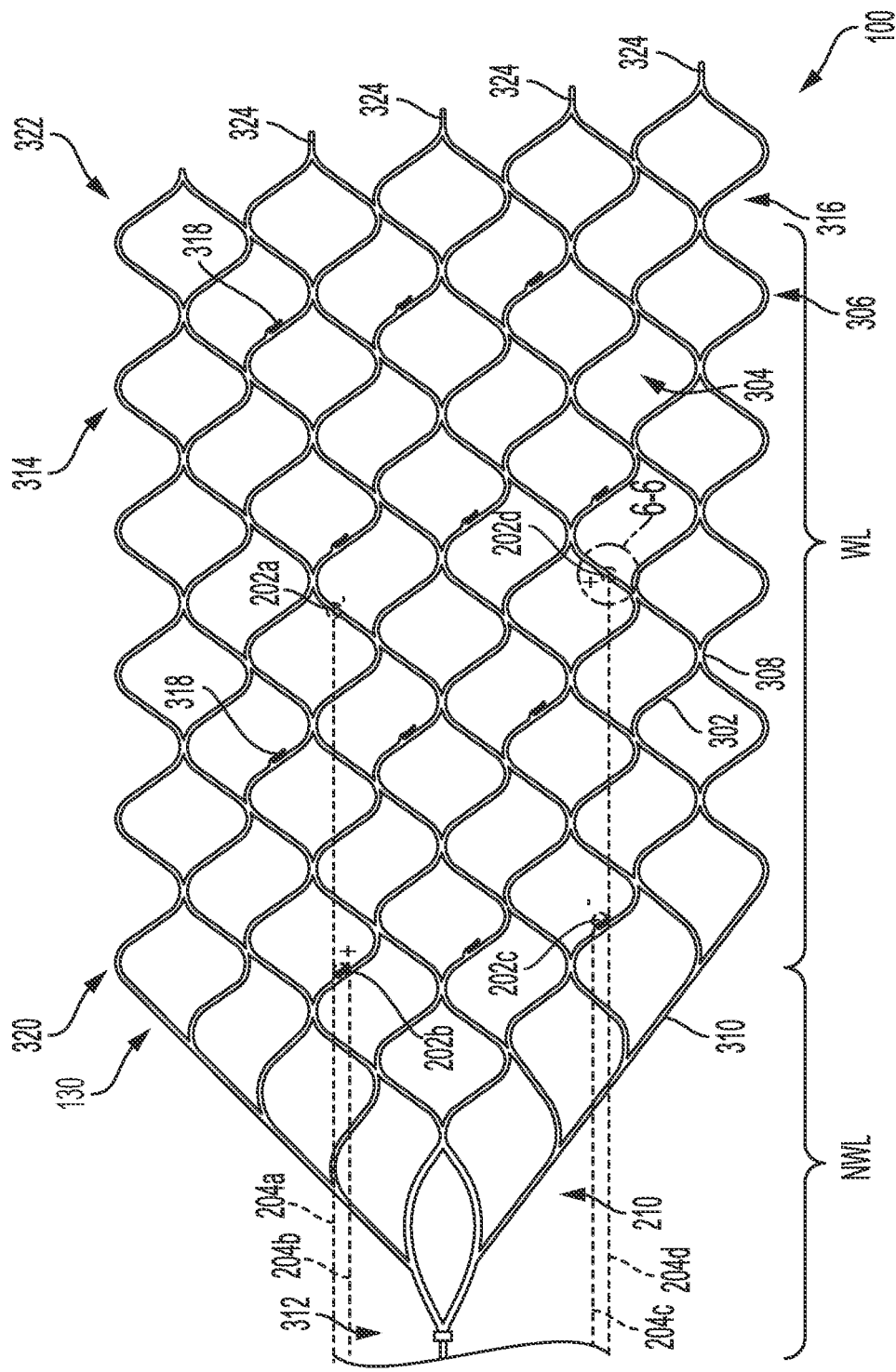
FIG. 3B illustrates another embodiment of an interventional element carrying a plurality of electrodes in an unrolled state.

FIG. 3B illustrates another example interventional element 100 carrying a plurality of electrodes 202 thereon in a "flat" view for ease of understanding. The configuration shown in FIG. 3B can be similar to that described previously with respect to FIG. 3A, except that, as shown in FIG. 3B, there are four leads 204*a-d* coupled respectively to four electrodes 202*a-d*. The first electrode 202*a* and the fourth electrode 202*d* take the form of conductive members coupled to a strut 302 of the interventional element 100, whereas the second electrode 202*b* and the third electrode 202*c* take the form of conductive members coupled to projections 318, similar to those described above with respect to FIG. 3A.

Figure 6:
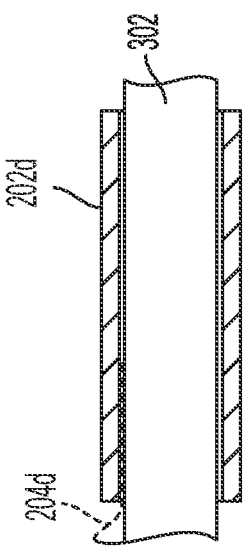
FIG. 6 is a detailed view of segment 6-6 shown in FIG. 3B.

A detailed view of the fourth electrode 202*d* mounted over the strut 302 is shown in FIG. 6. The electrode 202*d* can take the form of a coil, band, cap, or tube that fits over the strut 302. In various embodiments, the electrode 202*d* can extend around some or all of a circumference of the strut 302. The fourth lead 204*d* can be electrically coupled to the fourth electrode 202*d*. For example, the lead 204*d* can be soldered, welded, or otherwise adhered to and in electrical communication with the electrode 202*d*. In some embodiments, a distal end portion of the lead 204*d* extends into the space between the electrode 202*d* and the strut 302. According to some embodiments, the electrode 202*d* and/or the lead 204*d* may be in electrical communication with the material of the strut 302. In other embodiments, an insulative material may be disposed between the electrode 202*e* and the strut 302 (and/or an insulating material may be disposed between the lead 204*d* and the strut 302) such that current flowing through the electrode 202*d* and/or the lead 204*d* is inhibited from passing to the underlying strut 302 of the interventional element 100.

Referring back to FIG. 3B, the electrodes 202 can be coupled to terminals of a current generator via their respective leads 204 such that the second electrode 202*b* and the fourth electrode 202*d* serve as delivery electrodes (e.g., coupled to the positive terminal) and the first electrode 202*a* and the third electrode 202*c* serve as return electrodes (e.g., coupled to the negative terminal). In contrast to the configuration of FIG. 3A, in which delivery electrodes were disposed over a central portion of the interventional element 100 and return electrodes were positioned along distal tips, in the embodiment shown in FIG. 3B the return and delivery electrodes are both positioned over central portions (e.g., within the working length WL) of the interventional element 100. This configuration can provide a different charge distribution over the surface of the interventional element 100, for example by providing a shorter path between the delivery and return electrodes. Additionally, as shown in FIG. 3B, at least one delivery electrode 202*d* is positioned distally of at least one return electrode 202*c*, while at least one delivery electrode 202*b* is also positioned proximally of at least one return electrode 202*a*.

The embodiments shown in FIGS. 3A and 3B illustrate exemplary configurations of electrodes 202 and leads 204, however various other configurations are possible. For example, some or all of the electrodes can be mounted to the interventional element 100 at any suitable location, for example along a strut 302, a projection 318, a distally extending tip 324, or any other suitable position. Similarly, the number of electrodes 202, their respective polarities, and their relative positioning can be selected to achieve the desired charge distribution and other operating parameters.

Figure 7:
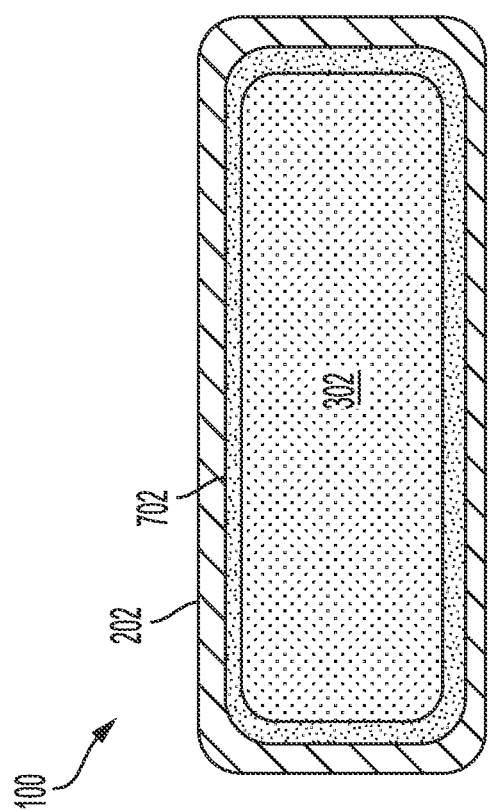
FIGS. 7-10 illustrate cross-sectional views of electrodes mounted on interventional elements in accordance with embodiments of the present technology.
Figure 8:
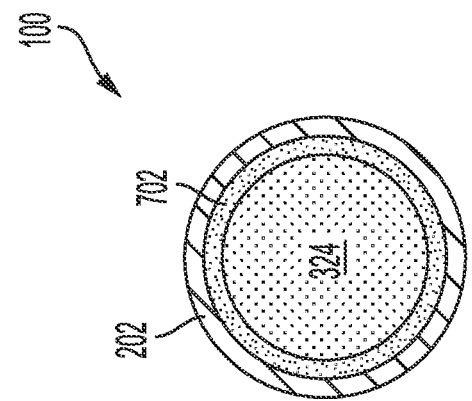

FIGS. 7 and 8 illustrate cross-sectional views of electrodes 202 mounted on interventional elements 100 with an intervening insulative material 702 disposed between the electrode 202 and the underlying portion of the interventional element in each instance. In the embodiment of FIG. 7, the portion of the interventional element 100 underlying the electrode 202 has a rectangular cross-section (for example, the strut 302), whereas in the embodiment of FIG. 8, the portion of the interventional element 100 underlying the electrode 202 has a circular cross-section (for example, the distally extending tip 324). These shapes are only exemplary, and in various embodiments the interventional element 100 can assume any suitable cross-sectional shape. In both FIGS. 7 and 8, the electrode 202 surrounds the segment of the interventional element 100, with an insulative material 702 disposed therebetween. The insulative material 702 can be, for example, Parylene, PTFE, polyimide, or any suitable electrically insulative material. As a result, current carried by the electrode 202 is not passed to the strut 302 or distally extending tip 324. Such insulated configurations may be employed for either delivery or return electrodes, as desired.

Figure 9:
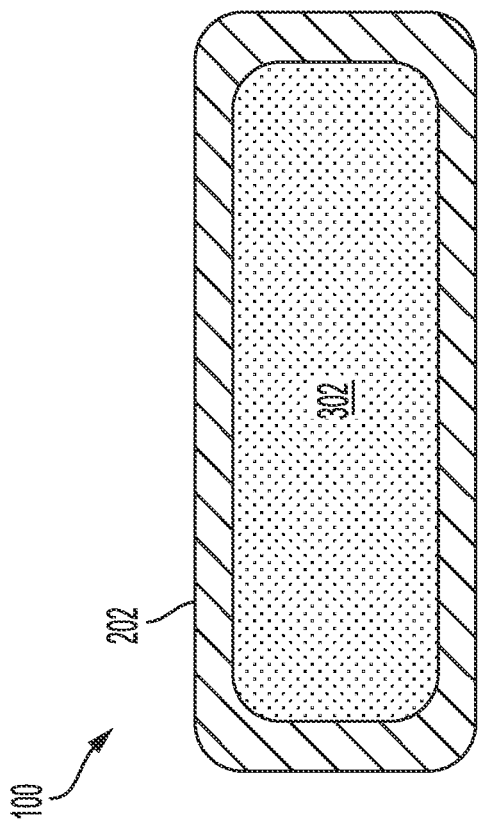
Figure 10:
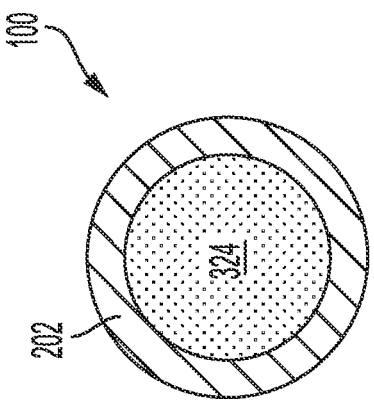

FIGS. 9 and 10 illustrates cross-sectional views of electrodes 202 mounted on interventional elements 100 so as to be in electrical communication with the interventional elements 100. Here there is no intervening insulative material, such that the electrode 202 is in direct contact and therefore in electrical communication with the underlying strut 302 or the distally extending tip 324 of the interventional element 100. In some embodiments one or more non-insulative (e.g., conductive) coatings can be disposed between the electrode 202 and the strut 302 or the distally extending tip 324 of the interventional element 100. In this configuration, current delivered to the electrode 202 passes to the underlying strut 302 or distally extending tip 324 of the interventional element 100, particularly if the interventional element 100 is made of an electrically conductive material such as stainless steel or nitinol. Such electrically coupled configurations may be employed for either delivery or return electrodes, as desired.

Figure 11:
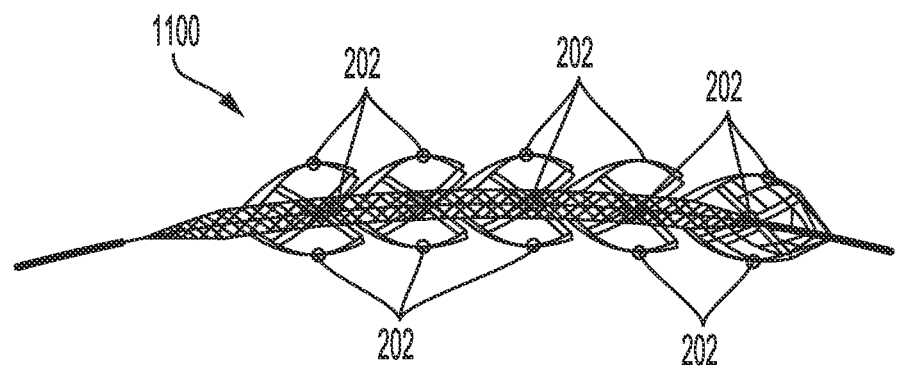
FIGS. 11-13 illustrate additional embodiments of interventional elements carrying electrodes.
Figure 12:
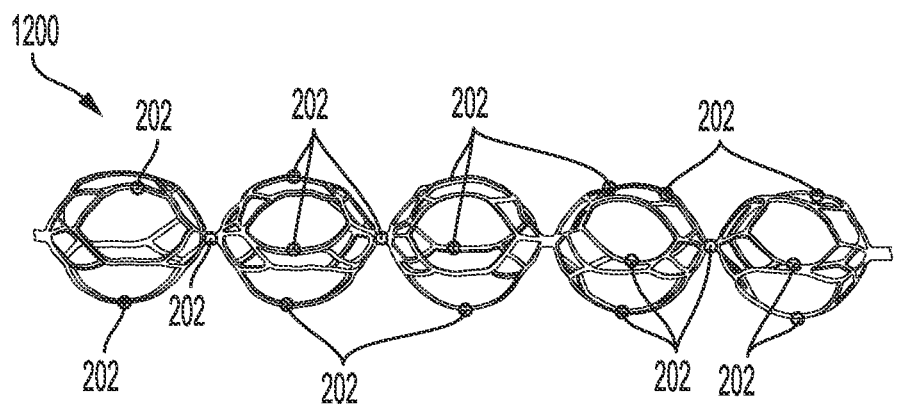
Figure 13:
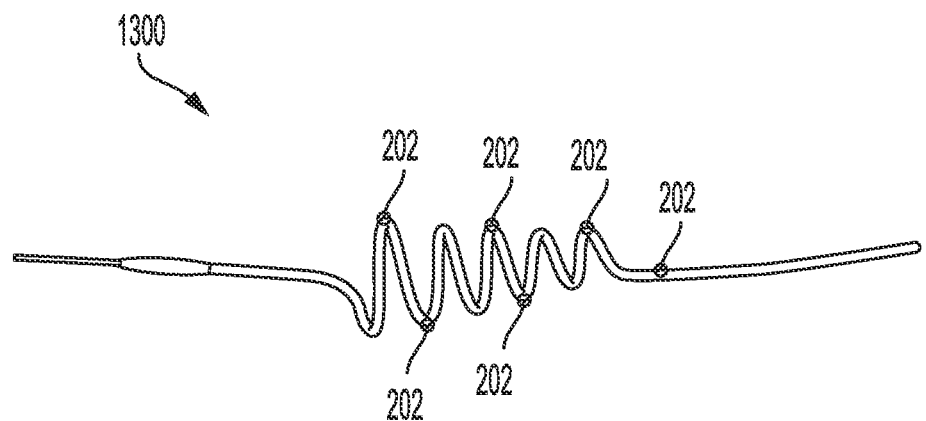

FIGS. 11-13 illustrate additional embodiments of interventional elements 1100, 1200, 1300 carrying a plurality of electrodes 202 thereon, which interventional elements and electrode arrangements can be similar to the various embodiments of the interventional element 100 and associated electrode arrangements described herein, except as otherwise specified. A plurality of leads (not shown) can be electrically coupled to the electrodes 202 to provide an electrical connection between a current generator and the individual electrodes 202 as described elsewhere herein. As shown in FIGS. 11-13, the interventional elements can take a number of different forms while benefiting from the electrically enhanced adhesion to clot material provided by the electrodes 202. For example, with respect to FIG. 11, the interventional element 1100 is a clot retrieval device with an inner tubular member and an outer expandable member having a greater diameter than the inner tubular member. The outer member can have radially outwardly extending struts defining inlet mouths configured to receive clot material therein. With respect to FIG. 12, the interventional element 1200 is another example of a clot retrieval device, in this instance comprising a plurality of interlinked cages having atraumatic leading surfaces and configured to expand radially outwardly to engage a thrombus. FIG. 13 illustrates another example interventional element 1300 in the form of a clot retrieval device, here comprising a coiled or helical member configured to be expanded into or distal to a thrombus, thereby engaging the thrombus between turns of the coil and facilitating removal from the body. In addition to these illustrative examples, the interventional element 100 can take other forms, for example a removal device, a thrombectomy device, a retrieval device, a braid, a mesh, a laser-cut stent, or any suitable structure.

II. SELECT EMBODIMENTS OF LEAD BUNDLE ASSEMBLIES FOR USE WITH THE TREATMENT SYSTEMS DISCLOSED HEREIN

As noted above, electrodes 202 carried by the interventional element 100 can be electrically coupled to an extracorporeal current generator 20 via longitudinally extending leads 204, which can be coupled or joined together via a proximally extending lead bundle assembly 205. In various embodiments, the lead bundle assembly 205 can extend parallel to but separate from the core member 11, or in some embodiments the lead bundle assembly can be coupled to or integrated with the core member 11. The leads 204 can be configured to be electrically coupled at their respective proximal end portions to a current generator (e.g., current generator 20; FIG. 1A) or other current source and to couple at their respective distal ends to one or more of the electrodes 202 coupled to the interventional element 100 as described elsewhere herein. In some embodiments, the leads 204 include both delivery electrode leads and return electrode leads, while in other embodiments the leads 204 include only delivery electrode leads, in which case one or more return electrodes can be separately coupled to a current generator (for example via an external needle or grounding pad, by being coupled to a catheter, or any other suitable configuration). Similarly, in some embodiments the leads 204 include only return electrode leads, with only return electrodes 202 carried by the interventional element 100. In such configurations, the delivery electrode may be provided elsewhere, for example coupled to a distal portion of a catheter, carried by another portion of the interventional element, or any other suitable arrangement.

Figure 14B:
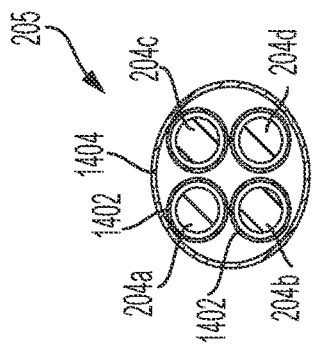
FIG. 14B is a cross-sectional view of the lead bundle assembly of FIG. 14A.
Figure 14A:
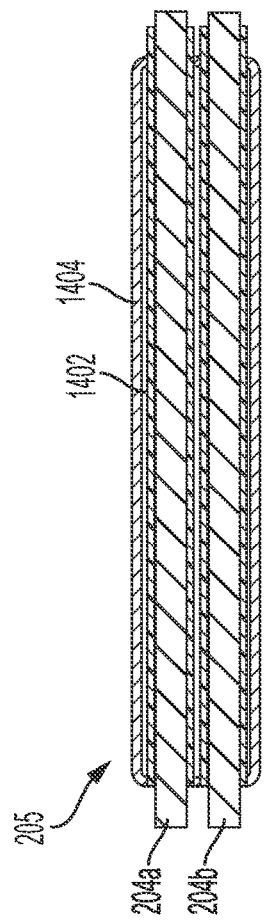
FIG. 14A is a side cross-sectional view of a lead bundle assembly in accordance with embodiments of the present technology.

FIG. 14A is a side cross-sectional view of a lead bundle assembly 205 in accordance with some embodiments, and FIG. 14B is a cross-sectional view of the assembly 205 shown in FIG. 14A. As shown in FIGS. 14A-B, the lead bundle assembly 205 includes four leads 204a-d extending longitudinally along the assembly 205. Although four leads are shown, in various embodiments there may be more or fewer leads, for example 1, 2, 3, 5, 6, 7, 8, 9, 10, or more leads. The lead bundle assembly 205 can have a length sufficient to extend between an extracorporeal current generator at a proximal end and an intravascular treatment site at the distal end. For example, the lead bundle assembly 205 can have a length of at least about 100 cm, at least about 125 cm, at least about 150 cm, or at least about 175 cm, or a length of between about 100 cm and 200 cm, or between about 150 cm and about 190 cm.

The leads 204 can each be exposed (e.g., not covered with insulative material) at a proximal end portion of the assembly 205 for coupling to a current generator (e.g., current generator 20; FIG. 1A). At a distal end portion of the lead bundle assembly 205, the leads 204 can extend distally away from the bundle assembly 205 separately, with each lead 204 extending towards a different electrode. This distally extending portion of the leads 204 (not shown here) can include an insulative material disposed over the individual leads 204, with an exposed distal end portion (e.g., leaving approximately 0.5-5 mm exposed) to facilitate coupling individual leads 204 to individual electrodes, as described above with respect to FIGS. 3A-6.

In at least some embodiments, the lead bundle assembly 205 includes a first insulating layer or material 1402 extending around each of the leads 204. The first insulating material 1402 can be, for example, polyimide any other suitable electrically insulating coating (e.g., PTFE, oxide, ETFE-based coatings, or any suitable dielectric polymer).

The first insulating material 1402 can circumferentially surround each lead 204, for example having a thickness of between about 0.00005" and about 0.0005", or about 0.0002". In some embodiments, the first insulating material 1402 extends along substantially the entire length of the leads 204 and the assembly 205. In some embodiments, the first insulating material 1402 separates and electrically insulates leads 204 from one another along substantially the entire length of the assembly 205. In some embodiments, the first insulating material 1402 does not cover the proximal-most portion of the leads 204, providing an exposed region of the leads 204 to which the current generator 20 (FIG. 1A) can be electrically coupled. In some embodiments, the first insulating material 1402 does not cover the distal-most portion of the leads 204, providing an exposed region of the leads 204 to which an electrode 202 (FIG. 3A) can be electrically coupled.

The lead bundle assembly 205 can additionally include a second insulating layer or material 1404 surrounding some or all of the leads 204 along at least a portion of their respective lengths. The second insulating material 1404 can be, for example, polyimide, or any other suitable electrically insulative coating (e.g., PTFE, oxide, ETFE based coatings or any suitable dielectric polymer). The insulating material 1404 can take the form of a substantially tubular member having a wall thickness of between about 0.00005" and about 0.0005", or about 0.0002". In some embodiments, the second insulating material 1404 does not cover the proximal-most portion of leads 204, providing an exposed region of the leads 204 to which the current generator 20 (FIG. 1A) can be electrically coupled. Distal to a distal end of the second insulating material 1404, the individual leads 204 (and optionally the surrounding first insulative material 1404) can extend distally towards individual electrodes 202, as noted previously.

In the embodiment of FIGS. 14A-B, the second insulating material 1404 defines an outer surface of the bundle assembly 205, which can be substantially cylindrical. In use, the bundle assembly 205 can be slidably advanced through a catheter (e.g., third catheter 12; FIG. 1A) alongside the core member 11. In some embodiments, the bundle assembly 205 can be coupled to the core member 11, for example being adhered together at one or more positions to prevent relative slidable movement. In other embodiments, the bundle assembly 205 and the core member 11 can remain separate and slidable and/or rotatable with respect to one another.

Figure 15B:
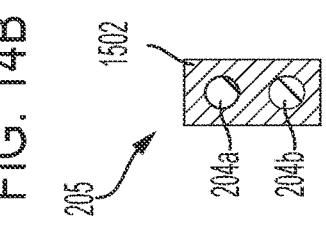
FIG. 15B is a cross-sectional view of the lead bundle assembly of FIG. 15A.
Figure 15A:
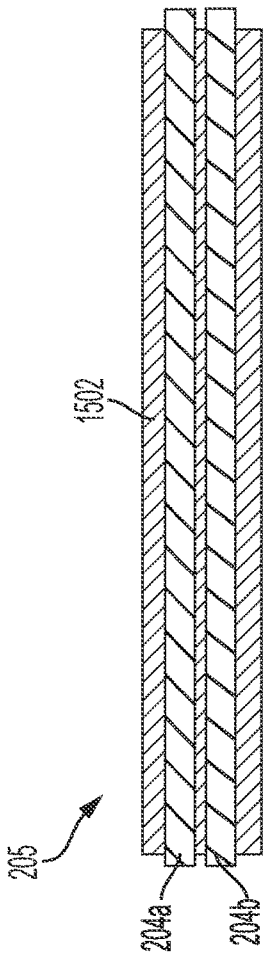
FIG. 15A is a side cross-sectional view of a lead bundle assembly in accordance with embodiments of the present technology.

FIG. 15A is a side cross-sectional view of a lead bundle assembly 205 in accordance with another embodiment, and FIG. 15B is a cross-sectional view of the assembly 205 shown in FIG. 15A. In this embodiment, two leads 204a and 204b are embedded within an insulative ribbon 1502. The ribbon can be made of an electrically insulative material, for example, polyimide, Parylene, PTFE, or any other suitable electrically insulative material, and can leave proximal and distal portions of the leads 204a and 204b exposed as described previously. As shown in FIG. 15B, the ribbon can have a substantially rectangular cross-section. The ribbon can have a thickness of between about 0.0005" to about 0.001" and a width of less than about 0.002".

Generally, the lead bundle assemblies depicted in FIGS. 14A-14B and 15A-15B can serve as the core member 11 without any additional structures or components, or with added structures such as a non-conducting core wire or shaft, a braided shaft or a surrounding (or central) tube, coil or braid. Such a tube can be laser-cut with a spiral or slotted pattern, or otherwise, to impart added flexibility where desired.

Figure 16B:
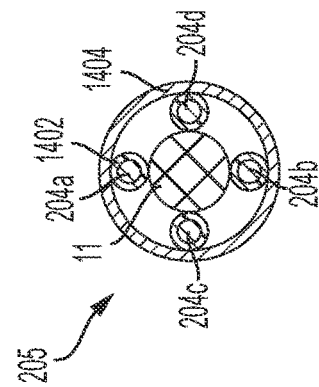
FIG. 16B is a cross-sectional view of the lead bundle assembly of FIG. 16A.
Figure 16A:
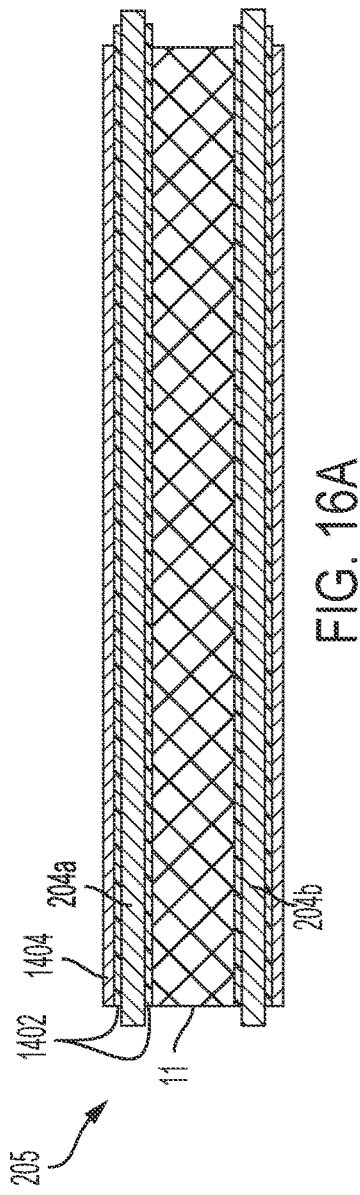
FIG. 16A is a side cross-sectional view of a lead bundle assembly in accordance with embodiments of the present technology.

FIG. 16A is a side cross-sectional view of a lead bundle assembly 205 in accordance with another embodiment, and FIG. 16B is a cross-sectional view of the assembly 205 shown in FIG. 16A. This embodiment can be similar to that of FIGS. 14A-14B, except that the assembly 205 is coaxially arranged around the core member 11 (which can comprise a wire, tube, braided shaft, etc. as described above). For example, each lead 204a-d can be coated with a first insulative material 1402 as described above with respect to FIGS. 14A-14B. However, in this embodiment, the leads 204 are disposed radially around the core member 11, and the surrounding second insulative material 1404 envelops both the leads 204 and the core member 11. As a result, the core member 11 and the leads 204 can be fixedly secured with respect to one another, and they can be slidably advanced through a surrounding catheter as a single unit.

IV. SELECT METHODS OF USE

Figure 17A:
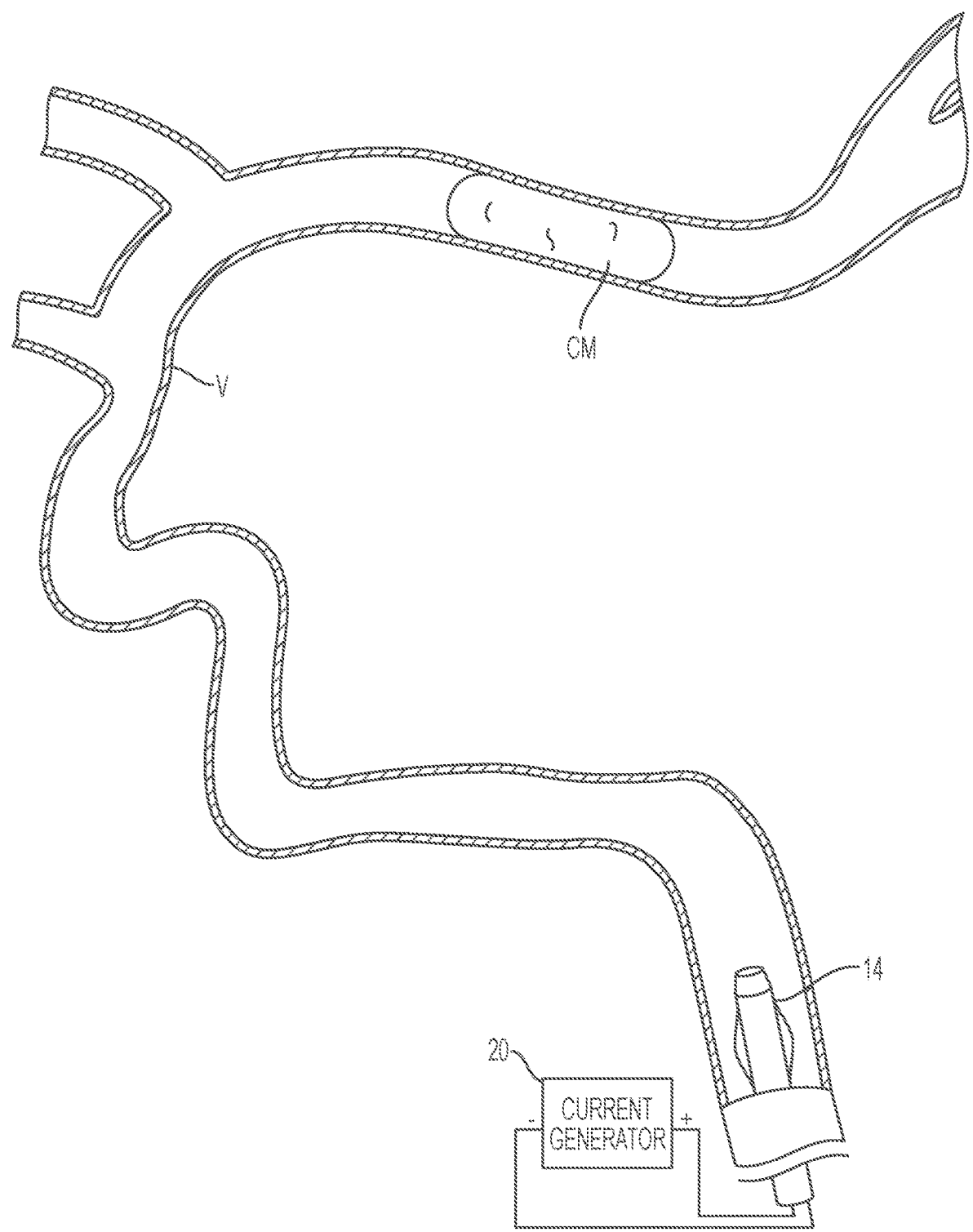
FIGS. 17A-17D illustrate a method of removing clot material from a blood vessel lumen using an electrically enhanced treatment system.
Figure 17B:
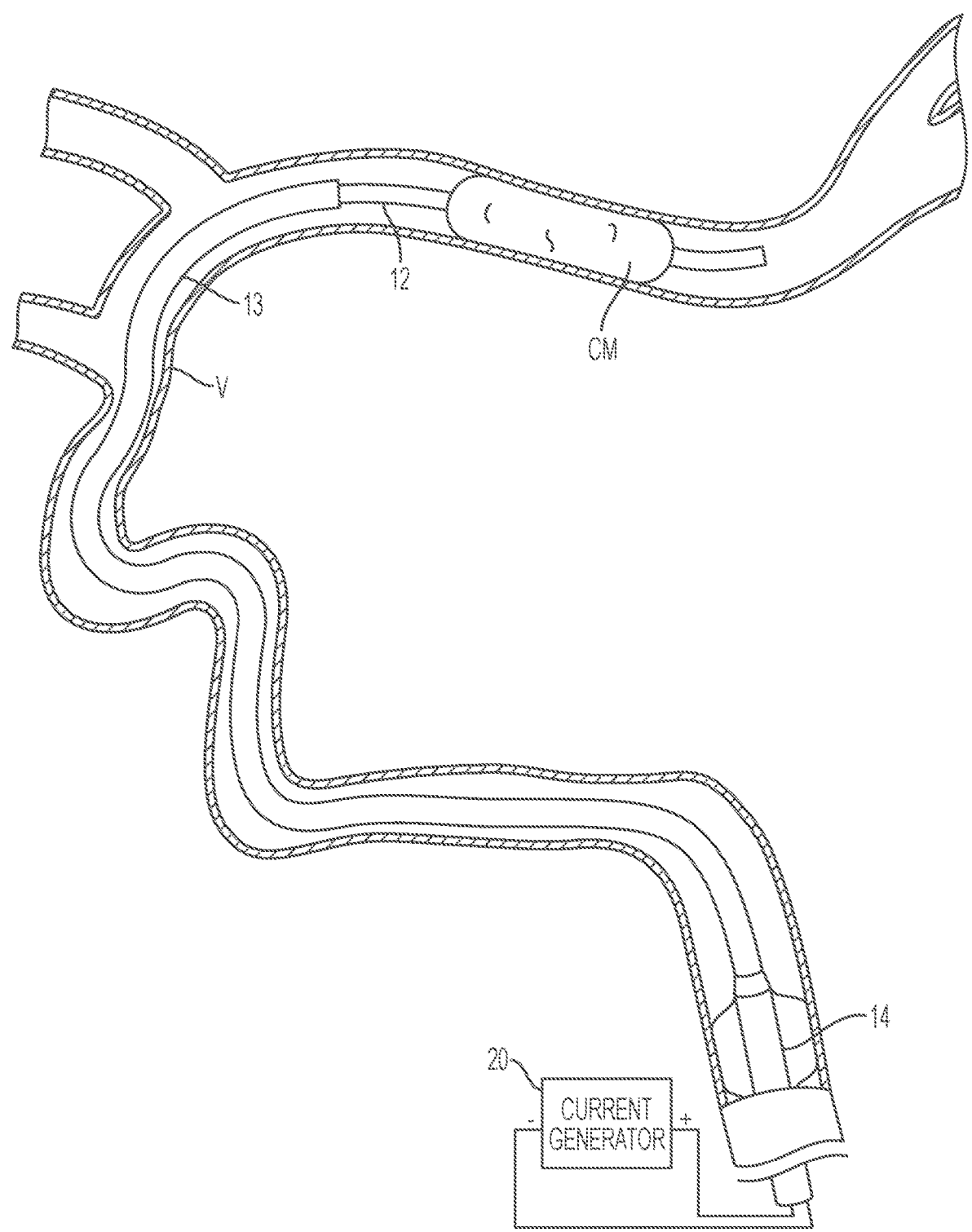

FIGS. 17A-17G illustrate a method of removing clot material CM from the lumen of a blood vessel V using the treatment system 10 of the present technology. As shown in FIG. 17A, the first catheter 14 can be advanced through the vasculature and positioned within the blood vessel such that a distal portion of the first catheter 14 is proximal of the clot material CM. As shown in FIG. 17B, the second catheter 13 may be advanced through the first catheter 14 until a distal portion of the second catheter 13 is at or proximal to the clot material CM. Next, the third catheter 12 may be advanced through the second catheter 13 so that a distal portion of the third catheter 12 is positioned at or near the clot material CM. In some embodiments, the third catheter 12 may be positioned such that a distal terminus of the third catheter 12 is distal of the clot material CM. The interventional element 100 may then be advanced through the third catheter 12 in a low-profile configuration until a distal terminus of the interventional element 100 is at or adjacent the distal terminus of the third catheter 12.

Figure 17C:
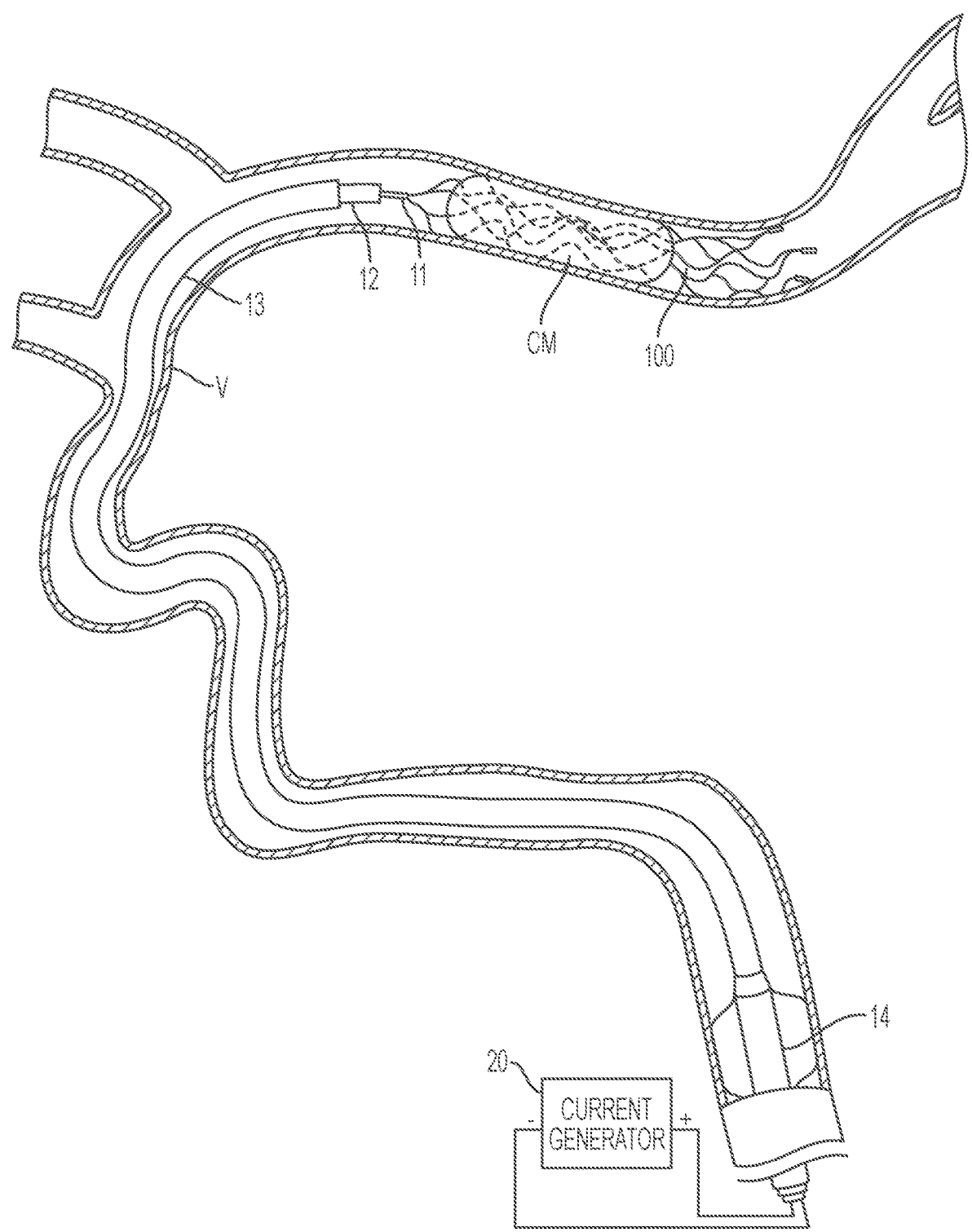

As shown in FIG. 17C, the third catheter 12 may be withdrawn proximally relative to the interventional element 100 to release the interventional element 100, thereby allowing the interventional element 100 to self-expand within the clot material CM. As the interventional element 100 expands, the interventional element 100 engages and/or secures the surrounding clot material CM, and in some embodiments may restore or improve blood flow through the clot material CM by pushing open a blood flow path therethrough. In some embodiments, the interventional element 100 may be expanded distal of the clot material CM such that no portion of the interventional element 100 is engaging the clot material CM while the interventional element 100 is in the process of expanding toward the vessel wall. In some embodiments, the interventional element 100 is configured to expand into contact with the wall of the vessel V, or the interventional element 100 may expand to a diameter that is less than that of the blood vessel lumen such that the interventional element 100 does not engage the entire circumference of the blood vessel wall.

Once the interventional element 100 has been expanded into engagement with the clot material CM, the interventional element 100 may grip the clot material CM by virtue of its ability to mechanically interlock with the clot material CM. The current generator 20, which is electrically coupled to the proximal end of the leads 204, can deliver a current to electrodes 202 carried by the interventional element 100 before or after the interventional element 100 has been released from the third catheter 12 into the blood vessel and/or expanded into the clot material CM. The interventional element 100 can be left in place or manipulated within the vessel V for a desired time period while the electrical signal is being delivered. Positive current delivered to the interventional element 100 via the electrodes 202 can attract negatively charged constituents of the clot material CM, thereby enhancing the grip of the interventional element 100 on the clot material CM. This allows the interventional element 100 to be used to retrieve the clot material CM with reduced risk of losing grip on the thrombus or a piece thereof, which can migrate downstream and cause additional vessel blockages in areas of the brain that are more difficult to reach.

In some methods of the present technology, a guidewire (not shown) may be advanced to the treatment site and pushed through the clot material CM until a distal portion of the guidewire is distal of the clot material CM. The guidewire may be advanced through one or more of the catheters 12-14 and/or one or more of the catheters 12-14 may be advanced over the guidewire. The guidewire may be insulated along at least a portion of its length (e.g., with Parylene, PTFE, etc.), with exposed portions permitting electrical communication with the current generator 20 and the interventional element 100. For example, in some embodiments a distal portion of the guidewire may be exposed, and the guidewire may be positioned at the treatment site such that the exposed portion of the guidewire is distal of the clot material CM. A proximal end of the guidewire may be coupled to the current generator such that the exposed portion of the guidewire functions as a return electrode. In some embodiments, the guidewire may be coupled to the positive terminal of the power source and the exposed portion functions as a delivery electrode. The guidewire may be used as a delivery or return electrode with any delivery or return electrode carried by any component of the treatment system (e.g., one or more of the first-third catheters 14, 13, 12, the interventional element 100, etc.).

In some methods, fluid may be delivered to the treatment site via the second catheter 13 and/or third catheter 12 while current is being delivered to the interventional element 100. Fluid delivery may occur before or while the interventional element 100 is engaging the thrombus, and may coincide with the entire duration of current delivery or just a portion thereof. In some instances, aspiration may be applied to the treatment site via the second catheter 13. For example, following deployment of the interventional element 100, the third catheter 12 can be retracted and removed from the lumen of the second catheter 13. The treatment site can then be aspirated via the second catheter 13, for example via a suction source such as a pump or syringe coupled to a proximal portion of the second catheter 13. In some embodiments, following expansion of the interventional element 100, the treatment site is aspirated concurrently with supplying electrical energy to the interventional element 100 via the current generator 20. By combining aspiration with the application of electrical energy, any newly formed clots (e.g., any clots formed that are attributable at least in part to the application of electrical energy), or any clot pieces that are broken loose during the procedure, can be pulled into the second catheter 13, thereby preventing any such clots from being released downstream of the treatment site. As a result, concurrent aspiration may permit the use of higher power or current levels delivered to the interventional element 100 without risking deleterious effects of new clot formation. Additionally, aspiration can capture any gas bubbles formed along the interventional element 100 during application of electrical energy to the interventional element 100, which can improve patient safety during the procedure.

In some embodiments, aspiration is applied while the interventional element 100 is retracted into the second catheter 13. Aspiration at this stage can help secure the clot material CM within the second catheter 13 and prevent any dislodged portion of the clot material CM from escaping the second catheter 13 and being released back into the vessel V. In various embodiments, the treatment site can be aspirated continuously before, during, or after delivering electrical signals to the interventional element 100 as well as before, during, or after retraction of the interventional element 100 into the second catheter 13.

At any time before, during, and/or after deployment of the interventional element 100, a flow arrest element (e.g., a balloon of a balloon-guide catheter or other suitable flow arrest element) may be deployed within the blood vessel proximal of the clot material CM to partially or completely arrest blood flow to the treatment site. In some methods, the flow arrest element may be deployed at a location along the blood vessel proximal of the clot material CM (for example, at a proximal portion of the internal carotid artery) and may remain inflated as the interventional element 100 is deployed and eventually withdrawn to remove the thrombus.

Figure 17D:
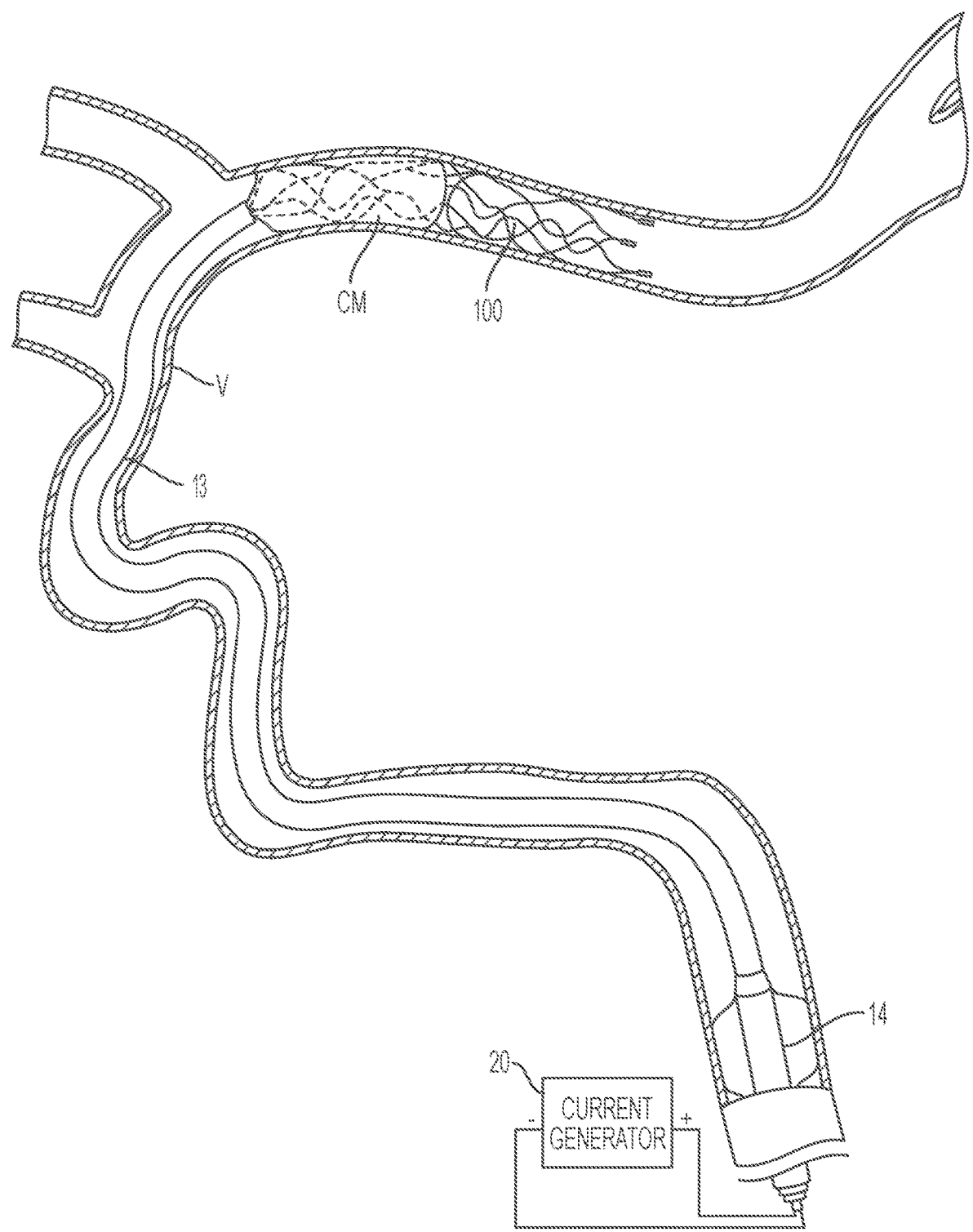

At least while the interventional element 100 is deployed and engaging the thrombus CM, electric current may be delivered to the interventional element 100 (e.g., via leads 204 and electrodes 202) to positively charge the interventional element 100, thereby enhancing clot adhesion to the interventional element 100. With reference to FIG. 17D, while the interventional element 100 is engaged with the clot material CM, the clot material CM can be removed. For example, the interventional element 100, with the clot material CM gripped thereby, can be retracted proximally (for example, along with the second catheter 13 and, optionally, the third catheter 12). The second catheter 13, interventional element 100, and associated clot material CM may then be withdrawn from the patient, optionally through one or more larger surrounding catheters. During this retraction, the interventional element 100 can grip the clot material CM electrically and/or electrostatically, e.g., via the application of current from a current generator as discussed herein. (As used herein with reference to gripping or retrieving thrombus or other vascular/luminal material, or to apparatus for this purpose, "electrical" and its derivatives will be understood to include "electrostatic" and its derivatives.) Accordingly, the interventional element 100 can maintain an enhanced or electrically and/or electrostatically enhanced grip on the clot material CM during retraction. In other embodiments, the current generator 20 may cease delivery of electrical signals to the electrodes 202 carried by the interventional element 100 prior to retraction of the interventional element 100 with respect to the vessel V. In some embodiments, the interventional element 100 and clot material CM form a removable, integrated thrombus-device mass wherein the connection of the thrombus to the device is electrically enhanced, e.g. via the application of current as discussed herein.

V. SELECT EMBODIMENTS OF WAVEFORMS FOR ELECTRICALLY ENHANCED RETRIEVAL

FIGS. 18A-18E show various electrical waveforms for use with the treatment systems of the present technology. Although the waveforms and other power delivery parameters disclosed herein can be used with the devices and methods described above with respect to FIGS. 1A-17D, the waveforms and other parameters are also applicable to other device configurations and techniques. For example, the return electrode can be provided along the catheter wall, as a separate conductive member extending within the catheter lumen, as a needle electrode provided elsewhere in the body, etc. In each of these device configurations, the power delivery parameters and waveforms can be beneficially employed to promote clot adhesion without damaging surrounding tissue. Additionally, although the waveforms and other power delivery parameters disclosed herein may be used for treating a cerebral or intracranial embolism, other applications and other embodiments in addition to those described herein are within the scope of the technology. For example, the waveforms and power delivery parameters disclosed herein may be used to electrically enhance removal of emboli from body lumens other than blood vessels (e.g., the digestive tract, etc.) and/or may be used to electrically enhance removal of emboli from blood vessels outside of the brain (e.g., pulmonary blood vessels, blood vessels within the legs, etc.).

As noted above, the treatment system can include a plurality of delivery electrodes and/or a plurality of return electrodes carried by an interventional element. In some embodiments, two or more delivery electrodes can be driven with the same waveforms. However, in some embodiments, two or more delivery electrodes can be driven with different waveforms to achieve the desired charge distribution characteristics at the interventional element 100.

Figure 18A:
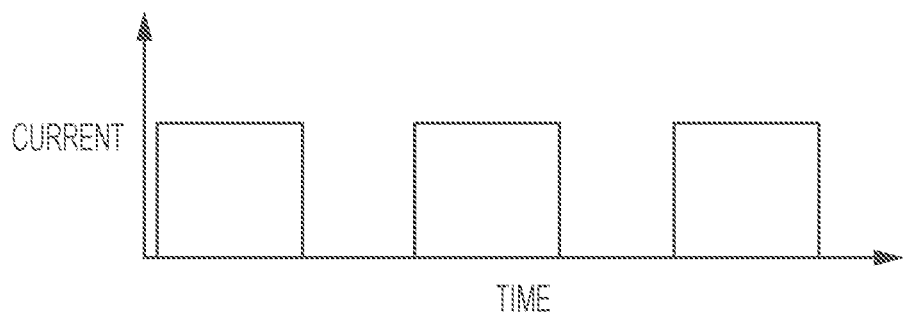
FIGS. 18A-18E illustrate sample waveforms for electrically enhanced removal of material from vessel lumens in accordance with one or more embodiments of the present disclosure.
Figure 18B:
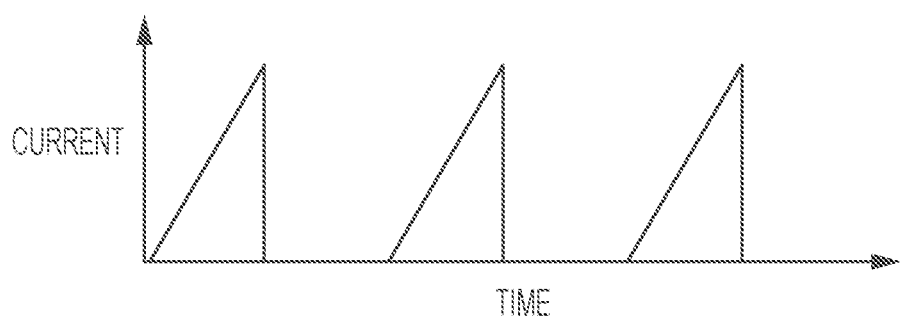
Figure 18C:
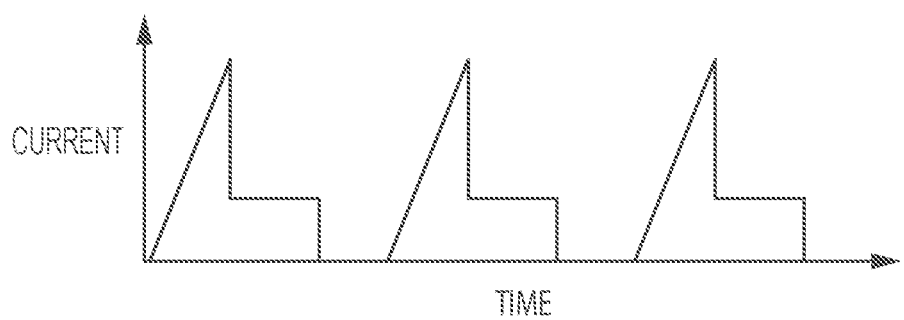
Figure 18D:
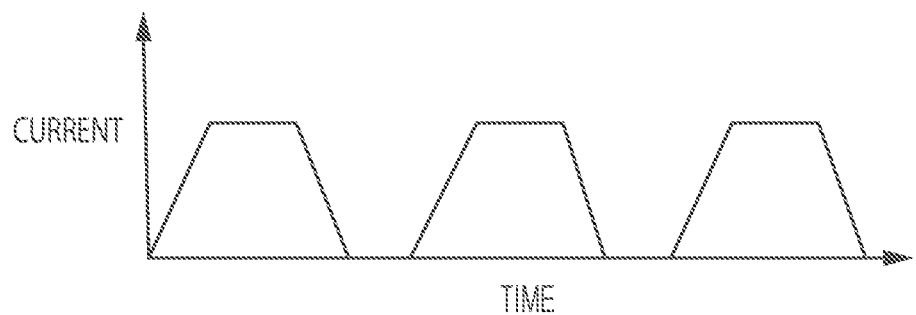
Figure 18E:
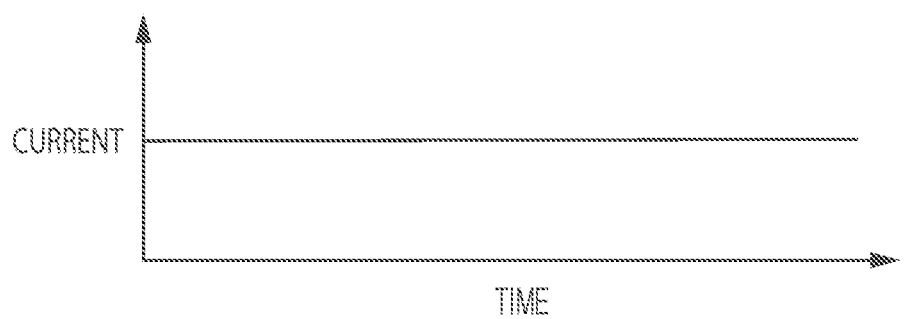

While applying a continuous uniform direct current (DC) electrical signal (as shown in FIG. 18E) to positively charge the interventional element can improve attachment to the thrombus, this can risk damage to surrounding tissue (e.g., ablation), and sustained current at a relatively high level may also be thrombogenic (i.e., may generate new clots). For achieving effective clot-grabbing without ablating tissue or generating substantial new clots at the treatment site, periodic waveforms have been found to be particularly useful. Without wishing to be bound by theory, the clot-adhesion effect appears to be most closely related to the peak current of the delivered electrical signal. Periodic waveforms can advantageously provide the desired peak current without delivering excessive total energy or total electrical charge. Periodic, non-square waveforms in particular are well suited to deliver a desired peak current while reducing the amount of overall delivered energy or charge as compared to either uniform applied current or square waveforms.

FIGS. 18A-18D illustrate various periodic waveforms that can be used with the devices and methods described above with respect to FIGS. 1A-17D, as well as with other devices and techniques. FIG. 18E illustrates a continuous uniform DC electrical signal which can also be used in some embodiments. Referring to FIGS. 18A-18D, electrical power can be delivered according to these waveforms as pulsed direct current. FIGS. 18A and 18B illustrate periodic square and triangular waveforms, respectively. These two waveforms have the same amplitude, but the triangular waveform is able to deliver the same peak current as the square waveform, with only half of the total charge delivered, and less total energy delivered. FIG. 18C illustrates another pulsed-DC or periodic waveform which is a composite of a square waveform and a triangular waveform. This superposition of a triangular waveform and a square waveform shown in FIG. 18C delivers additional efficacy compared to the triangular waveform of FIG. 18B while nonetheless delivering less overall energy than the square waveform of FIG. 18A. This is because the delivered energy is proportional to the square of current and the brief high peak in the composite waveform of FIG. 18C ensures that current is supplied without dispensing excessive energy. FIG. 18D illustrates yet another non-square waveform, in this case a trapezoidal waveform in which "ramp-up" and "ramp-down" portions at the beginning and end of each pulse provide periods of reduced current compared to square waveforms. In other embodiments, different non-square waveforms can be used, including a superposition of a square waveform with any non-square waveform, depending on the desired power delivery characteristics.

The waveform shape (e.g., pulse width, duty cycle, amplitude) and length of time can each be selected to achieve desired power delivery parameters, such as overall electrical charge, total energy, and peak current delivered to the interventional element and/or catheter. In some embodiments, the overall electrical charge delivered to the interventional element and/or catheter can be between about 30-1200 mC, or between about 120-600 mC. According to some embodiments, the total electrical charge delivered to the interventional element and/or catheter may be less than 600 mC, less than 500 mC, less than 400 mC, less than 300 mC, less than 200 mC, or less than 100 mC.

In some embodiments, the total energy delivered to the interventional element and/or aspiration catheter can be between about 0.75-24,000 mJ, or between about 120-24,000 mJ, or between about 120-5000 mJ. According to some embodiments, the total energy delivered to the interventional element and/or aspiration catheter may be less than 24,000 mJ, less than 20,000 mJ, less than 15,000 mJ, less than 10,000 mJ, less than 5,000 mJ, less than 4,000 mJ, less than 3,000 mJ, less than 2000 mJ, less than 1,000 mJ, less than 900 mJ, less than 800 mJ, less than 700 mJ, less than 600 mJ, less than 500 mJ, less than 400 mJ, less than 300 mJ, or less than 200 mJ, or less than 120 mJ, or less than 60 mJ, or less than 48 mJ, or less than 30 mJ, or less than 12 mJ, or less than 6 mJ, or less than 1.5 mJ.

In some embodiments, the peak current delivered can be between about 0.5-20 mA, or between about 0.5-5 mA. According to some embodiments, the peak current delivered may be greater than 0.5 mA, greater than 1 mA, greater than 1.5 mA, greater than 2 mA, greater than 2.5 mA, or greater than 3 mA.

The duration of power delivery is another important parameter that can be controlled to achieve the desired clot-adhesion effects without damaging tissue at the treatment site or generating new clots. In at least some embodiments, the total energy delivery time can be no more than 1 minute, no more than 2 minutes, no more than 3 minutes, no more than 4 minutes, or no more than 5 minutes. According to some embodiments, the total energy delivery time may be less about 30 seconds, less than about 1 minute, less than about 90 seconds, or less than about 2 minutes. As used herein, the "total energy delivery time" refers to the time period during which the waveform is supplied to the interventional element and/or catheter (including those periods of time between pulses of current).

The duty cycle of the applied electrical signal can also be selected to achieve the desired clot-adhesion characteristics without ablating tissue or promoting new clot formation. In some embodiments, the duty cycle can be between about 5% about 99% or between about 5% to about 20%. According to some embodiments, the duty cycle may be about 10%, about 20%, about 30%, about 40%, or about 50%. In yet other embodiments, a constant current may be used, in which the duty cycle is 100%. For 100% duty cycle embodiments, a lower time or current may be used to avoid delivering excess total energy to the treatment site.

Table 1 presents a range of values for power delivery parameters of different waveforms. For each of the conditions set forth in Table 1, a resistance of 1 kohm and a frequency of 1 kHz (for the Square, Triangle, and Composite conditions) was used. The Constant conditions represent a continuous and steady current applied for the duration, i.e. 100% duty cycle. The Peak Current 1 column represents the peak current for the corresponding waveform. For the Composite conditions, the Peak Current 2 column indicates the peak current of the second portion of the waveform. For example, referring back to FIG. 18C, Peak Current 1 would correspond to the current at the top of the triangular portion of the waveform, while Peak Current 2 would correspond to the current at the top of the square portion of the waveform.

ments the frequency of the waveform can be between 1 Hz and 1 MHz, between 1 Hz and 1 kHz, or between 500 Hz to 1 kHz.

VI. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily

TABLE 1

| Condition | Peak Current 1 (mA) | Peak Current 2 (mA) | Duty Cycle 1 (%) | Duty Cycle 2 (%) | Peak Voltage (V) | Pulse Width (ms) | Total Time (s) | Total Charge (mC) | Total Energy (@ R = 1000 ohm) (mJ) | Total Energy (@ R = 50 ohm) (mJ) |
|---|---|---|---|---|---|---|---|---|---|---|
| Constant 1 | 2 | 0 | 100 | 0 | 2 | n/a | 120 | 240 | 480 | 24 |
| Constant 2 | 2 | 0 | 100 | 0 | 2 | n/a | 60 | 120 | 240 | 12 |
| Constant 3 | 10 | 0 | 100 | 0 | 10 | n/a | 60 | 600 | 6000 | 300 |
| Constant 4 | 20 | 0 | 100 | 0 | 20 | n/a | 60 | 1200 | 24000 | 1200 |
| Constant 5 | 10 | 0 | 100 | 0 | 10 | n/a | 120 | 1200 | 12000 | 600 |
| Constant 6 | 1 | 0 | 100 | 0 | 1 | n/a | 120 | 120 | 120 | 6 |
| Constant 7 | 0.5 | 0 | 100 | 0 | 1 | n/a | 120 | 60 | 30 | 1.5 |
| Constant 8 | 0.5 | 0 | 100 | 0 | 1 | n/a | 60 | 30 | 15 | 0.75 |
| Square 1 | 10 | 0 | 10 | 0 | 10 | 0.1 | 120 | 120 | 1200 | 60 |
| Square 2 | 4 | 0 | 50 | 0 | 4 | 0.5 | 120 | 240 | 960 | 48 |
| Square 3 | 20 | 0 | 10 | 0 | 20 | 0.1 | 120 | 240 | 4800 | 240 |
| Square 4 | 20 | 0 | 10 | 0 | 20 | 0.1 | 60 | 120 | 2400 | 120 |
| Square 5 | 10 | 0 | 10 | 0 | 10 | 0.1 | 60 | 60 | 600 | 30 |
| Triangle 1 | 10 | 0 | 10 | 0 | 10 | 0.1 | 120 | 60 | 1200 | 60 |
| Triangle 2 | 20 | 0 | 10 | 0 | 20 | 0.1 | 120 | 120 | 4800 | 240 |
| Composite 1 | 20 | 1 | 10 | 20 | 20 | 0.3 | 120 | WL | 4824 | 264 |
| Composite 2 | 10 | 2 | 10 | 20 | 10 | 0.3 | 120 | 108 | 1296 | 156 |

As seen in Table 1, the periodic waveforms (Square, Triangle, and Composite conditions) achieve higher peak currents with lower overall charge delivered than the corresponding Constant conditions. For example, in condition Constant 4, a peak current of 20 mA corresponds to a total energy delivered of 24,000 mJ, while condition Square 3 delivers a peak current of 20 mA with a total energy of only 4,800 mJ. Conditions Triangle 2 and Composite 1 similarly deliver lower total energy while maintaining a peak current of 20 mA. Since clot-adhesion appears to be driven by peak current, these periodic waveforms can therefore offer improved clot adhesion while reducing the risk of damaging tissue at the treatment site or promoting new clot formation. Table 1 also indicates that the Triangle and Composite conditions achieve higher peak currents with lower overall charge delivered than the corresponding Square conditions. For example, condition Square 3 has a peak current of 20 mA and a total charge delivered of 240 mC, while condition Triangle 2 has a peak current of 20 mA but a total charge delivered of only 120 mC, and condition Composite 1 has a peak current of 20 mA and a total charge delivered of only WL mC. As such, these non-square waveforms provide additional benefits by delivering desirable peak current while reducing the overall charge delivered to the treatment site.

Although Table 1 represents a series of waveforms with a single frequency (1 kHz), in some embodiments the frequency of the pulsed-DC waveforms can be controlled to achieve the desired effects. For example, in some embodiobscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Unless otherwise indicated, all numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising," and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A medical device comprising:
an elongate core member having a distal portion configured to be intravascularly positioned at a treatment site within a blood vessel lumen;
an interventional element coupled to the distal portion of the core member, the interventional element comprising:
a body that is expandable from a first configuration to a second configuration;
a first radiopaque element coupled to the body within a working length of the body, the first radiopaque element comprising an electrically conductive material; and
a second radiopaque element coupled to the body within a non-working length of the body, the second radiopaque element comprising an electrically conductive material;
a first electrically conductive lead having a distal portion electrically coupled to the first radiopaque element and a proximal portion configured to be electrically coupled to a current source such that the first radiopaque element is configured to serve as a delivery electrode; and
a second electrically conductive lead having a distal portion electrically coupled to the second radiopaque element and a proximal portion configured to be electrically coupled to the current source such that the second radiopaque element is configured to serve as a return electrode.

2. The device of claim 1, wherein the body comprises an electrically conductive material.

3. The device of claim 1, wherein the body is in electrical communication with the first radiopaque element.

4. The device of claim 1, wherein the first conductive lead extends proximally along the core member.

5. The device of claim 1, further comprising:
a plurality of third radiopaque elements coupled to the body within the working length of the body, each comprising an electrically conductive material; and
a plurality of third electrically conductive leads, each having a distal portion electrically coupled to one of the plurality of third radiopaque elements and having a proximal portion configured to be electrically coupled to the current source.

6. The device of claim 5, wherein the plurality of third radiopaque elements are configured to serve as additional delivery electrodes.

7. The device of claim 1, wherein the first radiopaque element comprises a radiopaque marker.

8. The device of claim 1, wherein the interventional element comprises a thrombectomy device.

9. A system comprising:
the device of claim 1; and
a current source electrically coupled to the first and second electrically conductive leads.

10. A medical device comprising:
a thrombectomy element comprising:
a body configured to engage a thrombus;
a first electrically conductive radiopaque element coupled to the body within a working length of the body configured to serve as a delivery electrode; and
a second electrically conductive radiopaque element coupled to the body within a non-working length of the body configured to serve as a delivery electrode;
a first electrically conductive lead in electrical communication with the first radiopaque element, the first lead configured to be electrically coupled to a current source; and
a second electrically conductive lead in electrical communication with the second radiopaque element, the second lead configured to be electrically coupled to the current source.

11. The device of claim 10, wherein the body comprises an electrically conductive material.

12. The device of claim 10, wherein the body is in electrical communication with the first radiopaque element.

13. The device of claim 10, further comprising:
a plurality of third electrically conductive radiopaque elements coupled to the body; and
a plurality of third electrically conductive leads, each electrically coupled to one of the plurality of third radiopaque elements and being configured to be electrically coupled to the current source.

14. The device of claim 13, wherein a first set of the plurality of third radiopaque elements are configured to serve as additional delivery electrodes, and wherein a second set of the third plurality of radiopaque elements are configured to serve as additional return electrodes.

15. The device of claim 14, wherein the delivery electrodes are disposed within a working length of the body, and wherein the return electrodes are disposed within a non-working length of the body.

16. The device of claim 13, wherein the plurality of third radiopaque elements are configured to serve as additional delivery electrodes.

17. The device of claim 10, wherein the thrombectomy element comprises a stent retriever.

* * * * *